(12) United States Patent
Liu

(10) Patent No.: US 10,689,654 B2
(45) Date of Patent: Jun. 23, 2020

(54) BIVALENT SIRNA CHIMERAS AND METHODS OF USE THEREOF

(71) Applicant: Augusta University Research Institute, Inc., Augusta, GA (US)

(72) Inventor: Hong Yan Liu, Martinez, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 0 days.

(21) Appl. No.: 15/726,851

(22) Filed: Oct. 6, 2017

(65) Prior Publication Data

US 2018/0105815 A1 Apr. 19, 2018

Related U.S. Application Data

(60) Provisional application No. 62/409,579, filed on Oct. 18, 2016.

(51) Int. Cl.
| | | |
|---|---|---|
| *C12N 15/115* | (2010.01) | |
| *C12N 15/113* | (2010.01) | |
| *A61K 47/54* | (2017.01) | |
| *A61K 31/713* | (2006.01) | |
| *A61K 45/06* | (2006.01) | |

(52) U.S. Cl.
CPC .......... *C12N 15/115* (2013.01); *A61K 31/713* (2013.01); *A61K 45/06* (2013.01); *A61K 47/549* (2017.08); *C12N 15/113* (2013.01); *C12N 15/1138* (2013.01); *C12N 2310/14* (2013.01); *C12N 2310/16* (2013.01); *C12N 2310/344* (2013.01); *C12N 2310/3519* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | | | |
|---|---|---|---|---|
| 2011/0197292 | A1* | 8/2011 | Sullenger | C12N 15/111 800/13 |
| 2012/0124683 | A1* | 5/2012 | Sullenger | C12N 15/111 800/13 |
| 2013/0129719 | A1* | 5/2013 | Giangrande | C12N 15/1135 424/133.1 |
| 2015/0122516 | A1* | 5/2015 | Prescott | A01B 1/00 172/371 |
| 2016/0076036 | A1* | 3/2016 | Rossi | C12N 15/111 514/44 A |
| 2016/0348113 | A1* | 12/2016 | Rossi | C12N 15/111 |

OTHER PUBLICATIONS

Stauber, R. H., et al., "Nuclear and Cytoplasmic Survivin: Molecular Mechanism, Prognostic, and Therapeutic Potential", Cancer Res 67, 5999-6002 (2007).
Summer, H., et al., "Denaturing Urea Polyacrylamide Gel Electrophoresis (Urea PAGE)", J Vis Exp (32), e1485, (2009).
Traish, A. M., et al., "Epidermal Growth Factor Receptor Expression Escapes Androgen Regulation in Prostate Cancer: A Potential Molecular Switch for Tumour Growth", British Journal of Cancer 101, 1949-1956 (2009).
Tuerk, C., et al., "Systematic Evolution of Ligands by Exponential Enrichment: RNA Ligands to Bacteriophage T4 DNA Polymerase", Science 249, 505-510 (1990).
Wang, T., et al., "EpCAM Aptamer-Mediated Survivin Silencing Sensitized Cancer Stem Cells to Doxorubicin in a Breast Cancer Model", Theranostics 5, 1456-1472 (2015).
Wheeler, L. A., et al., "Inhibition of HIV Transmission in Human Cervicovaginal Explants and Humanized Mice Using CD4 Aptamer siRNA Chimeras", J Clin Invest 121, 2401-2412 (2011).
Whitehead, K. A., et al., "Knocking Down Barriers: Advances in siRNA Delivery", Nat Rev Drug Discov 8, 129-138 (2009).
Wu, S. Y., et al., "RNAi Therapies: Drugging the Undruggable", Sci Transl Med 6, 240ps7, (2014).
Wullner, U., et al., "Cell-Specific Induction of Apoptosis by Rationally Designed Bivalent Aptamer-siRNA Transcripts Silencing Eukaryotic Elongation Factor 2", Curr Cancer Drug Targets 8, 554-565 (2008).
Wyatt, A. W., et al., "The Diverse Heterogeneity of Molecular Alterations in Prostate Cancer Identified Through Next-Generation Sequencing", Asian J Androl 15, 301-308 (2013).
Zhang, M., et al., "Survivin Mediates Resistance to Antiandrogen Therapy in Prostate Cancer", Oncogene 24, 2474-2482 (2005).
Zhou, J., et al., "Novel Dual Inhibitory Function Aptamer-siRNA Delivery System for HIV-1 Therapy", Mol Ther 16, 1481-1489 (2008).
Zhou, J., et al., "Development of Cell-Type Specific Anti-HIV gp120 Aptamers for siRNA Delivery", J Vis Exp (52), e2954, (2011).
Zhou, J., et al., "Current Progress of RNA Aptamer-Based Therapeutics", Front Genet 3, 234, (2012).
Altieri, D. C., "Opinion-Survivin, Cancer Networks and Pathway-Directed Drug Discovery", Nature Reviews Cancer 8, 61-70 (2008).
Altieri, D. C., "Targeting Survivin in Cancer", Cancer Lett 332, 225-228 (2013).
Baek, D., et al., "The Impact of MicroRNAs on Protein Output", Nature 455, 64-71 (2008).
Bernstein, E., et al., "Role for a Bidentate Ribonuclease in the Initiation Step of RNA Interference", Nature 409, 363-366 (2001).
Cataldo, V.D., et al., "A. Treatment of Non-Small-Cell Lung Cancer with Erlotinib or Gefitinib", N Engl J Med 364, 947-955 (2011).
Chang, S. S., et al., "Prostate-Specific Membrane Antigen is Produced in Tumor-Associated Neovasculature", Clin Cancer Res 5, 2674-2681 (1999).
Chang, S. S., et al., "Five Different Anti-Prostate-Specific Membrane Antigen (PSMA) Antibodies Confirm PSMA Expression in Tumor Associated Neovasculature", Cancer Res 59, 3192-3198 (1999).

(Continued)

*Primary Examiner* — Sean McGarry
(74) *Attorney, Agent, or Firm* — Smith, Gambrell & Russell, LLP

(57) ABSTRACT

A bivalent siRNA chimera platform capable of efficiently delivering and silencing two or more genes in vivo or in vitro is provided. Methods of using the bivalent siRNA chimeras for selectively targeting cells to down-regulate the expression of multiple genes are also provided.

15 Claims, 20 Drawing Sheets
Specification includes a Sequence Listing.

(56) References Cited

OTHER PUBLICATIONS

Chang, Y. S., et al., "EGF Receptor Promotes Prostate Cancer Bone Metastasis by Downregulating miR-1 and Activating TWIST1", Cancer Res 75, 3077-3086 (2015).
Chong, C. R., et al., "The Quest to Overcome Resistance to EGFR-Targeted Therapies in Cancer", Nat Med 19, 1389-1400 (2013).
Ciardiello, F., et al., "Interaction Between the Epidermal Growth Factor Receptor (EGFR) and the Vascular Endothelial Growth Factor (VEGF) Pathways: A Rational Approach for Multi-Target Anticancer Therapy", Annals of Oncology 17, Vii109-Vii114 (2006).
Cochran, J. R., et al., "Receptor Clustering and Transmembrane Signaling in T Cells", Trends Biochem Sci 26, 304-310 (2001).
Dassie, J. P., et al. "Systemic Administration of Optimized Aptamer-siRNA Chimeras Promotes Regression of PSMA-Expressing Tumors", Nat Biotechnol 27, 839-849 (2009).
Dassie, J. P., et al., "Current Progress on Aptamer-Targeted Oligonucleotide Therapeutics", Ther Deliv 4, 1527-1546 (2013).
De Luca, A., et al., "The Role of the EGFR Signaling in Tumor Microenvironment", J Cell Physiol 214, 559-567 (2008).
Di Lorenzo, G., et al., "Expression of Epidermal Growth Factor Receptor Correlates with Disease Relapse and Progression to Androgenindependence in Human Prostate Cancer", Clin Cancer Res 8, 3438-3444 (2002).
Ellington, A. D., et al., "In Vitro Selection of RNA Molecules that Bind Specific Ligands", Nature 346, 818-822 (1990).
Grate, D., et al., "Laser-Mediated, Site-Specific Inactivation of RNA Transcripts", Proc Natl Acad Sci USA 96, 6131-6136 (1999).
Hannon, G. J., "RNA Interference", Nature 418, 244-251 (2002).
Harding, F. A., et al., "The Immunogenicity of Humanized and Fully Human Antibodies: Residual Immunogenicity Resides in the CDR Regions", MAbs 2, 256-265 (2010).
Haringsma, H. J., et al., "mRNA Knockdown by Single Strand RNA is Improved by Chemical Modifications", Nucleic Acids Res 40, 4125-4136 (2012).
Herrmann, A., et al., "CTLA4 Aptamer Delivers STAT3 siRNA to Tumor-Associated and Malignant T Cells", J Clin Invest 124, 2977-2987 (2014).
Howe, L. R., et al., "Targeting the HER/EGFR/ErbB Family to Prevent Breast Cancer", Cancer Prev Res (Phila) 4, 1149-1157 (2011).
Hussain, A. F., et al., "An Aptamer-siRNA Chimera Silences the Eukaryotic Elongation Factor 2 Gene and Induces Apoptosis in Cancers Expressing Alphavbeta3 Integrin", Nucleic Acid Ther 23, 203-212 (2013).
Jensen, S. A., et al., "Spherical Nucleic Acid Nanoparticle Conjugates as an RNAi-Based Therapy for Glioblastoma", Sci Transl Med 5, 209ra152 (2013).
Jinek, M., et al., "A Three-Dimensional View of the Molecular Machinery of RNA Interference", Nature 457, 405-412 (2009).
Judge, A. D., et al., "Sequence-Dependent Stimulation of the Mammalian Innate Immune Response by Synthetic siRNA", Nat Biotechnol 23, 457-462 (2005).
Kosaka, T., et al., "Angiotensin II Type 1 Receptor Antagonist as an Angiogenic Inhibitor in Prostate Cancer", Prostate 67, 41-49 (2007).
Larsen, A. K., et al., "Targeting EGFR and VEGF(R) Pathway Cross-Talk in Tumor Survival and Angiogenesis", Pharmacol Ther 131, 80-90 (2011).
Lens, S. M., et al., "The Case for Survivin as Mitotic Regulator", Curr Opin Cell Biol 18, 616-622 (2006).
Liu, H. Y., et al., "A Universal Protein Tag for Delivery of SiRNA-Aptamer Chimeras", Sci Rep 3, 3129 (2013).
Liu, H. Y., et al., "Co-Targeting EGFR and Survivin with a Bivalent Aptamer-Dual siRNA Chimera Effectively Suppresses Prostate Cancer", Sci Rep 6, 30346 (2016).
Ma, J. B., et al., "Structural Basis for Overhang-Specific Small Interfering RNA Recognition by the PAZ Domain", Nature 429, 318-322 (2004).
Martinez-Veracoechea, F. J., et al., "Designing Super Selectivity in Multivalent Nano-Particle Binding", Proc Nat Acad Sci USA 108, 10963-10968 (2011).
McNamara, J. O. 2nd, et al., "Cell Type-Specific Delivery of siRNAs with Aptamer-siRNA Chimeras", Nat Biotechnol 24, 1005-1015 (2006).
Meacham, C. E., et al., "Heterogeneity and Cancer Cell Plasticity", Nature 501, 328-337 (2013).
Misale, S., et al., "Vertical Suppression of the EGFR Pathway Prevents Onset of Resistance in Colorectal Cancers", Nat Commun 6, 8305 (2015).
Moore, M. J., et al. "Erlotinib. Plus Gemcitabine Compared with Gemcitabine Alone in Patients with Advanced Pancreatic Cancer: A Phase III Trial of the National Cancer Institute of Canada Clinical Trials Group", J Clin Oncol 25, 1960-1966 (2007).
Neff, C. P., et al., "An Aptamer-siRNA Chimera Suppresses HIV-1 Viral Loads and Protects from Helper CD4(+) T Cell Decline in Humanized Mice", Sci Transl Med 3, 66ra6, (2011).
Pastor, F., et al., "Induction of Tumour Immunity by Targeted Inhibition of Nonsense-Mediated mRNA Decay", 465, 227-U114 (2010).
Pecot, C. V., et al., "RNA Interference in the Clinic: Challenges and Future Directions", Nat Rev Cancer 11, 59-67 (2011).
Pieken, W. A., et al., "Kinetic Characterization of Ribonuclease-Resistant 2'-Modified Hammerhead Ribozymes", Science 253, 314-317 (1991).
Pore, N., et al., "EGFR Tyrosine Kinase Inhibitors Decrease VEGF Expression by Both Hypoxia-Inducible Factor (HIF)-1-Independent and HIF-1-Dependent Mechanisms", Cancer Res 66, 3197-3204 (2006).
Porter, A. G., et al., "Emerging Roles of Caspase-3 in Apoptosis", Cell Death Differ 6, 99-104 (1999).
Qureshi, O. S., et al., "Constitutive Clathrin-Mediated Endocytosis of CTLA-4 Persists During T Cell Activation", J Bol Chem 287, 9429-9440 (2012).
Rauch, A., et al., "Survivin and YM155: How Faithful is the Liaison?", Biochimica Et Biophysica Acta-Reviews on Cancer 1845, 202-220 (2014).
Schlomm, T., et al., "Clinical Significance of Epidermal Growth Factor Receptor Protein Overexpression and Gene Copy Number Gains in Prostate Cancer", Clin Cancer Res 13, 6579-6584 (2007).
Semenza, G. L., "Targeting HIF-1 for Cancer Therapy", Nat Rev Cancer 3, 721-732 (2003).
Siegel, R. L., et al., "Cancer Statistics, 2015", CA Cancer J Clin 65, 5-29 (2015).
Siomi, H., et al., "On the Road to Reading the RNA-Interference Code", Nature 457, 396-404 (2009).
Sioud, M., "Single-Stranded Small Interfering RNA are More Immunostimulatory than their Double-Stranded Counterparts: A Central Role for 2'-Hydroxyl Uridines in Immune Responses", Eur J Immunol 36, 1222-1230 (2006).

* cited by examiner

Detection of IFNα from human peripheral blood mononuclear cells (PBMCs) in the presence of PSEP by ELISA

| Standard IFNα(ng/ml) | OD450 | PSEP(μM) | OD450 5h | 24h |
|---|---|---|---|---|
| 0 | 0.316 ± 0.010 | 0 | 0.352 ± 0.014 | 0.288 ± 0.014 |
| 0.549 | 0.341 ± 0.015 | 0.1 | 0.329 ± 0.001 | 0.362 ± 0.006 |
| 1.646 | 0.485 ± 0.008 | 0.2 | 0.298 ± 0.01 | 0.280 ± 0.006 |
| 4.938 | 0.792 ± 0.007 | 0.5 | 0.314 ± 0.008 | 0.314 ± 0.004 |
| 14.81 | 1.396 ± 0.012 | 1.0 | 0.297 ± 0.001 | 0.276 ± 0.002 |
| 44.44 | 2.640 ± 0.008 | 4.0 | 0.298 ± 0.011 | 0.373 ± 0.005 |
| 13.33 | 3.211 ± 0.016 | | | |

BIVALENT SIRNA CHIMERAS AND METHODS OF USE THEREOF

CROSS-REFERENCE TO RELATED APPLICATION

This application claims benefit of and priority to U.S. Provisional Patent Application No. 62/409,579 filed on Oct. 18, 2016, which is incorporated by reference in its entirety.

STATEMENT REGARDING FEDERALLY SPONSORED RESEARCH

This invention was made with government support under W81XWH-15-1-0333 awarded by the Department of Defense. The government has certain rights in the invention.

FIELD OF THE INVENTION

The invention is generally directed to siRNA compositions for inhibiting gene expression in targeted cells.

REFERENCE TO SEQUENCE LISTING

The Sequence Listing submitted Oct. 6, 2017, as a text file named "064466_021.txt" created on Oct. 6, 2017, and having a size of 8 kbytes is hereby incorporated by reference pursuant to 37 C.F.R. § 1.52(e)(5).

BACKGROUND OF THE INVENTION

Prostate cancer (PCa) is the most common cancer in American men, contributing to 220,800 new cases and 27,540 deaths in 2015 (Siegel, et al., *CA Cancer J Clin*, 65: 5-29 (2015)). Current therapies, although temporarily reducing cancer-related complications, do not have significant survival benefits. Particularly, single-agent treatment only exhibits limited activity in clinical settings, which may be attributed to the intrinsic and complex heterogeneity of a tumor (Meacham, et al., *Nature*, 501: 328-337 (2013)). Indeed, abnormalities in multiple tumor suppressors and oncogenes have been identified in PCa3, which may account for the failure of most targeted therapies that selectively block a single oncogenic molecule or signaling pathway.

Activation of EGFR signaling has been shown to increase cancer cell proliferation, enhance tumor vascularization and promote metastasis (De Luca, et al., *J Cell Physiol*, 214: 559-567 (2008); Howe, et al., *Cancer Prev Res (Phila)*, 4: 1149-1157 (2011)). EGFR overexpression is associated with castration-resistant and high-risk PCa, as well as PCa bone metastasis (Schlomm, et al, *Clin Cancer Res*, 13: 6579-6584 (2007); Di Lorenzo, et al., *Clin Cancer Res*, 8: 3438-3444 (2002); Chang, et al., *Cancer Res*, 75: 3077-3086 (2015); Traish, et al., *British Journal of Cancer*, 101: 1949-1956 (2009)). EGFR inhibitors (e.g. erlotinib, gefitinib) have been used to treat prostate, pancreatic, lung, colorectal and head and neck cancers (Cataldo, et al., *N Engl J Med*, 364: 947-955 (2011); Moore, et al., *J Clin Oncol*, 25: 1960-1966 (2007)). However, the benefit of EGFR inhibitors is temporary and can be quickly counteracted by acquired resistance (Chong, et al., *Nat Med*, 19: 1389-1400 (2013)). Combination treatment, on the other hand, may restore the sensitivity of tumors to EGFR inhibitors. For example, the combined use of anti-MEK and anti-EGFR inhibitors can overcome the resistance of colorectal cancer[13], and the combination of anti-EGFR and anti-VEGF agents have shown success and some have been approved for the clinical trials (Ciardiello, et al., *Annals of Oncology*, 17: Vii109-Vii114 (2006)).

Survivin, a member of the inhibitor of apoptosis (IAP) protein family (Lens, et al., *Curr Opin Cell Biol*, 18: 616-622 (2006)), plays a pivotal role in the progression of PCa and other solid tumors. Its overexpression has been correlated to recurrence, metastasis and therapeutic resistance (Altieri, et al., *Cancer Lett*, 332: 225-228 (2013); Stauber, et al., *Cancer Res*, 67: 5999-6002 (2007); Zhang, et al., *Oncogene*, 24: 2474-2482 (2005)). Survivin has been actively pursued as an ideal target for cancer treatment. However, the portfolio of efficient survivin antagonists is small. Currently available inhibitors of survivin (such as YM155) have modest activity and are associated with side effects (Rauch, et al., *Biochimica Et Biophysica Acta-Reviews on Cancer*, 1845: 202-220 (2014)). The lack of survivin-directed antagonists also reflects the limitation of current drug design, since only those molecules expressed on cell surface or having enzymatic activity are considered to be druggable. It remains challenging to discover small molecule inhibitors against cytoplasmic proteins (such as survivin).

Heterogeneity is an intrinsic characteristic of human cancer, particularly at advanced stages. Combination therapy to target several oncogenic pathways simultaneously, therefore, may have better efficacy in retarding or eradicating tumors. Small molecule drug combination usually shows some efficacy initially, but reaches a plateau with increased toxicity and quickly developed drug resistance. For example, although current kinase inhibitor combinations show efficacy and certain targeting, most kinase inhibitors tend to target multiple kinases (low specificity), and combinations of different kinases may more easily cause overlapping toxicities. Combinations of monoclonal antibodies are usually more specific but have limitations in antagonizing intracellular targets/signaling and high immunogenicity due to their membrane impermeability and recognition by host as foreign.

Therefore it is an object of the invention to provide compositions and methods for selectively targeting cells to inhibit gene expression.

It is another object to provide compositions and methods for selectively targeting virally infected cells to inhibit gene expression.

It is another object of the invention to provide compositions and methods for selective targeting cells to inhibit multiple genes in the cells.

It is still another object of the invention to provide compositions and methods for reducing tumor burden in a subject.

It is still another object of the invention to provide compositions and methods for treating cancer or viral infections.

SUMMARY OF THE INVENTION

A bivalent siRNA chimera platform capable of efficiently delivering and silencing two or more genes in vivo or in vitro is provided. Methods of using the bivalent siRNA chimeras for selectively targeting cells to down-regulate the expression of multiple genes are also provided.

Currently, most chimeras are designed as the fusion of one aptamer with one siRNA (Dassie, et al., *Nat Biotechnol*, 27: 839-849 (2009); Herrmann, et al., *J Clin Invest*, 124: 2977-2987 (2014); Zhou, et al., *Mol Ther*, 16: 1481-1489 (2008); Hussain, et al., *Nucleic Acid Ther*, 23: 203-212 (2013); Wheeler, et al., *J Clin Invest*, 121: 2401-2412 (2011)).

Importantly, simultaneous delivery of multiple siRNAs has not been reported. In one embodiment, the bivalent siRNA chimera delivers at least two siRNAs against two or more different genes to cells expressing a specific cell surface protein or secreting a specific protein into the microenvironment of the cell. The genes to be down-regulated include, but are not limited to oncogenes, proto-oncogenes, tumor specific antigens, and viruses.

One embodiment provides a bivalent siRNA chimera that contains two siRNAs that down-regulate expression of EGFR and survivin, respectively. The bivalent siRNA chimera also contains two aptamers on either end of the chimera that specifically bind to a cell surface protein, for example a tumor specific antigen or a viral antigen. Using multiple aptamers specific to a cell surface protein increases efficiency of delivering the siRNAs to the targeted cell. The disclosed bivalent siRNA chimeras are processed by cellular RNA interference machinery (Siomi, et al., *Nature*, 457: 396-404 (2009)) to produce separate and active siRNAs that inhibit expression of two different genes. In one embodiment, the chimera can simultaneously silence EGFR and survivin in vitro and in vivo. The data in the Examples demonstrates a profound efficacy against PCa growth through the induction of apoptosis and inhibition of angiogenesis. Co-delivery of at least two siRNAs in one chimera represents a new approach for combination therapy of using siRNA molecules.

In one embodiment, the aptamers of the bivalent siRNA chimeras specifically bind to prostate-specific membrane antigen (PSMA). Thus, a method for treating prostate cancer is provided which includes administering to a subject in need thereof and effective amount of bivalent siRNA chimera having aptamers that specifically bind to PSMA and siRNA constructs that are processed to produce siRNA that inhibits expression of EGFR and survivin.

Another embodiment provides a pharmaceutical composition containing one or more different bivalent siRNA chimeras in an amount effective to down down-regulate at least two different genes in a target cell.

Another embodiment provides a method for treating a viral infection by administering to a subject in need thereof an effective amount of a bivalent siRNA chimera that targets virally infected cells and down regulates two or more genes of the virus infecting the subject.

One embodiment provides a bivalent aptamer-siRNA chimera comprising nucleic acid sequences having at least 80, 85, 90, 95, 99, or 100% sequence identity to SEQ ID Nos:1, 5 and 8.

BRIEF DESCRIPTION OF THE DRAWINGS

FIG. 1A shows the structure of PSMA aptamer-survivin siRNA-EGFR siRNA-PSMA aptamer (PSEP) formed of SEQ ID NOs:1, 5, and 8. PSEP chimera includes a bivalent PSMA aptamer and two siRNAs specific to survivin and EGFR. Each antisense strand of siRNAs has a 2-nt overhang at the 3' end. FIG. 1B shows the proposed mechanism of gene silencing. Upon internalization, PSEP chimera is recognized by Dicer. Dicer will process chimera into 21-nt siRNA duplex intermediates. The duplexes are unwound and recruited to the RNA-induced silencing complex (RISC) where Ago proteins mediate targeted mRNA silencing. FIG. 1C shows the results of the Dicer assay. PSEP chimera was treated with human recombinant dicer for 6 h or 12 h. The digestion patterns were resolved with 3.5% agarose gel electrophoresis. The gel images showed that the small siRNA was produced after PSEP was treated with dicer. The cropped gel is used in the main figures. FIG. 1D shows the evaluation of serum stability by denaturing 5% acrylamide/8 M urea gel electrophoresis. Unmodified or 2' F-modified PSEP was incubated with PBS buffer containing 50% human serum for 1-4 h, and 2' F-modified PSEP was incubated with PBS containing 50% human serum for 24 h. PSEP intensity was measured with ImageJ. FIG. 1E shows the comparison of internalization of bivalent aptamer chimera vs monovalent control. Cy3-labeled PSEP, PSEM or MSEM were added into C4-2 cells for 2 h at 37° C. LysoTracker Green was used to show lysosomes and endosomes. Confocal laser scanning microscopy was performed to show cell binding and internalization. Scale bar, 20 μm. FIG. 1F shows the quantification of the binding and internalization from confocal microscopy by ImageJ. 30-50 cells for each chimera are evaluated. * * P<0.01. FIG. 1G shows the detection of internalization. C4-2 cells were treated with Cy3-labeled PSEP, PSEM or MSEM for 2 h at 37° C. Cells were washed with DPBS plus 0.5 M NaCl to remove surface bound RNAs. The amount of fluorescently labeled chimeras that internalized into cells was measured using flow cytometry.

FIG. 2A shows the evaluation of PSMA expression by Western blot. FIG. 2B shows the knockdown of PSMA using siRNA and qualification of PSMA expression. Data are mean±SEM (n=3). * * P<0.01. FIG. 2C shows the cell binding assay by flow cytometry. C4-2, PC3, BXPC3 and T-24 cells were incubated with Cy3-labeled PSEP and Cy3-labeled MSEM, and detected by flow cytometry. Unstained cells are shown in solid blue, MSEM staining cells are shown in green line, and PSEP staining cells are shown in black line. FIG. 2D shows the detection of knockdown of EGFR and survivin by Western blot. The cropped blots are displayed in the main figures, and the black lines surrounding blots indicate the cropping lines. FIG. 2E shows the quantification of EGFR and survivin protein levels normalized by β-tubulin. The results are the mean±SEM from three independent experiments. * P<0.05. FIG. 2F shows the detection of cleaved Caspase-3 by Western blot. The cropped blots are displayed in the main figures. FIG. 2G shows the quantification of Western blot FIG. 2F. Protein levels are normalized to β-tubulin. Data show mean±SEM of three independent experiments. * P<0.05, * * P<0.01. FIG. 2H shows the comparison of cytotoxicity of chimeras. C4-2 cells were treated with PSEP, PSP, PEP or MSEM at the varying concentrations. The results are representative of three independent experiments. FIG. 2I shows C4-2 cells were treated with PSMA aptamer alone, simply mixed siRNAs specific to survivin and EGFR, and PSMAapt-CON (scrambled siRNA). The results are representative of three independent experiments. FIG. 2J shows the cell type-specific cytotoxicity assay. Cell lines were treated with the varying concentrations of PSEP for 72 h. The results are representative of three independent experiments.

FIG. 3A shows that flow cytometry showed the increased populations at early-apoptosis (Annexin V+PI−) and at late apoptosis (Annexin V+PI+). The stage movement confirmed that apoptosis occurs upon PSEP treatment. Consistently FIG. 3B shows epi-fluorescence microscopy showed apoptosis pattern: cell shrinkage and increased signals of Annexin V (green) and PI (red). Scale bar, 100 μm.

FIG. 4A shows the direct observation of the tumors after treatments with PBS, PSMAapt-CON and PSEP. PSEP treated tumors are significantly smaller than PBS- and PSMAapt-CON-treated tumors. Remarkably, in contrast to the dark and bloody tumors in control groups, tumors in PSEP group have changed to much less bloody with lighter color. FIG. 4B shows representative tumor-bearing mouse imaging. With whole-body imaging, tumors on control mice (PBS and PSMAapt-CON) are blue, in contrast, tumors post PSEP treatment are grey and white under the skin. FIG. 4C shows corresponding tumor growth curves. After C4-2 cells were implanted into athymic mice, PSEP, PBS or PSMAapt-CON was intraperitoneally injected to mice. Following the treatment, tumors were measured using a digital caliper twice a week. (n=4, *P<0.05).

FIG. 5A shows H&E staining and CD31 IHC to identify blood vessels. H&E staining exhibited that tumor tissues in controls (PBS and PSMAapt-CON) are enriched with high-density blood vessels, which span entire tumors, in contrast, after PSEP treatment, tumors have much less density of blood vessels. IHC assay for CD31 expression further revealed that blood vessel density of tumors has been significantly reduced upon PSEP treatment. Furthermore, detection of HIF1a expression at tissue (FIG. 5B) and at cultured cells. FIG. 5C shows IHC staining of tumor tissues revealed the significant decrease of HIF1α in vivo, and Western blot showed that the reduction of HIF1α in C4-2 cells was observed after PSEP treatment. The cropped blots are displayed in the main figures, and the black lines surrounding blots indicate the cropping lines. FIG. 5D shows detection of VEGF-A secretion from C4-2 cells. C4-2 cells were treated with PSEP for 72 h. The culture supernatants were measured for VEGF-A secretion by ELISA. PSEP can significantly inhibit the expression of VEGF-A in C4-2 cells at a dose-dependent manner. *P<0.05, and **P<0.01.

FIG. 7A shows histological evaluation of the tissue damages after treatment. The organs (heart, lung, liver, kidney, brain, muscle, spleen, and intestine) were removed for H& E staining. Compared with naïve (no tumor implant), the organs from PSEP treated xenografts do not exhibit significant histological change. FIG. 7B shows monitoring of mouse body weights following PSEP treatment. PSEP treated mice have a significant increase of body weight. FIG. 7C shows the detection of interferon response. IFNα from normal human peripheral blood mononuclear cells upon treatment with PSEP was measured. The expression of in culture supernatants were quantified with human IFNα ELISA Kit. There was no detectable IFNα in the test range from 100 nM up to 4 μM, which represents 8 folds as high as the dose used in the experiments.

DETAILED DESCRIPTION OF THE INVENTION

I. Definitions

Figure 1A:
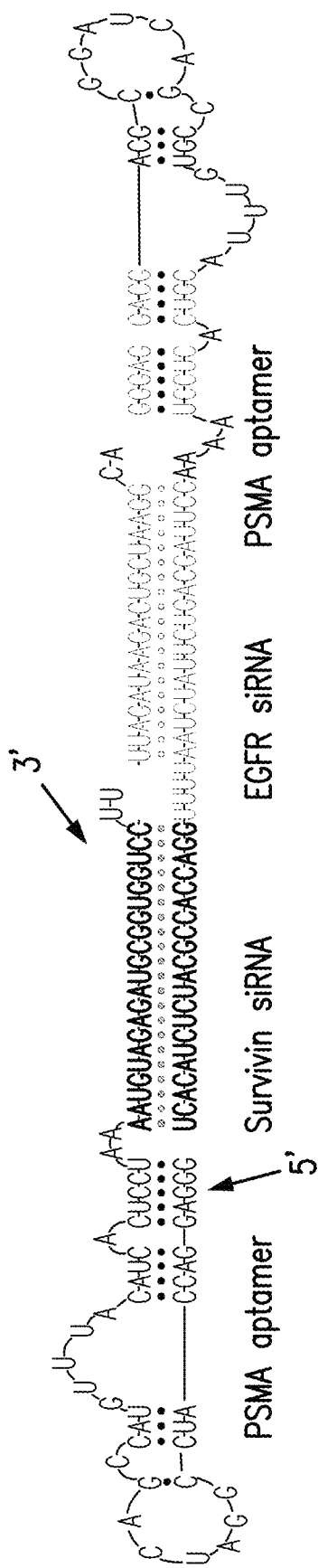
FIGS. 1A-1G refer to the design and characterization of bivalent aptamer-dual siRNA chimera.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the term "effective amount" in the context of the administration of a therapy to a subject refers to the amount of a therapy that achieves a desired prophylactic or therapeutic effect.

As used herein, the term "in combination" refers to the use of more than one therapies (e.g., one or more prophylactic and/or therapeutic agents). The use of the term "in combination" does not restrict the order in which therapies are administered to a subject with a disease or disorder, or the route of administration. A first therapy (e.g., a prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disease or disorder or a symptom thereof.

As used herein, the terms "subject" and patient" are used interchangeably and refer to an animal. In a specific embodiment, such terms refer to a mammal such as a non-primate (e.g., cows, pigs, horses, cats, dogs, rats etc.) and a primate (e.g., monkey and human), most preferably a human. In certain embodiments, such terms refer to a non-human animal (e.g., a non-human animal such as a pig, horse, cow, cat, or dog). In some embodiments, such terms refer to a pet or farm animal. In specific embodiments, such terms refer to a human.

As used herein, the terms "treat", "treating" and "treatment" in the context of the administration of a bivalent siRNA chimera to a subject refer to the beneficial effects that a subject derives from the therapy. In certain embodiments, treatment of a subject with a bivalent siRNA chimera achieves one, two, three, four, or more of the following effects: (i) reduction or amelioration the severity of disease or symptom associated therewith; (ii) reduction in the duration of a symptom associated with a disease; (iii) prevention of the progression of a disease or symptom associated therewith; (iv) regression of a disease or symptom associated therewith; (v) prevention of the development or onset of a symptom associated with a disease; (vi) prevention of the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy.

The term "oncogene" refers to a gene that can in some circumstances transform a cell into a cancerous cell or a gene that promotes the survival of a cancer cell.

II. Aptamer-siRNA Chimeras

A bivalent siRNA chimera platform capable of efficiently delivering and silencing two or more genes in vivo or in vitro is provided. Methods of using the bivalent siRNA chimeras for treating cancer, for example prostate cancer, are also provided.

A. Bivalent siRNA Chimera Design

In one embodiment, the aptamer-siRNA chimeras contain at least two siRNAs that inhibit or reduce expression of two or more oncogenes (FIG. 1A). The aptamer-siRNA chimera also contains an aptamer on each end of the chimera that specifically binds to a tumor cell surface protein are provided. Exemplary tumor cell surface proteins include oncogenes and proto-oncogenes. The structure of chimera can be processed by cellular RNAi machinery to produce the active siRNAs for each targeted oncogene (FIG. 1A). Bivalent aptamers offer much enhanced cargo internalization and target specificity.

In one embodiment, the two tandem siRNAs are separated by a linker. The linker can be about 2-10, 3-9, or preferably about 4 nucleotides. An exemplary linker is four uracils ("U"). The linker helps to warrant the cleavage with dicer but not mixing two genes, since dicer is able to measure and cut 21-25-nt RNA duplex. The sequence complementarity among PSMA aptamer, survivin siRNA and EGFR siRNA, was examined and no significant complementary sequences were found, ensuring the correct folding by annealing. The size of the exemplary PSMA aptamer-Survivin siRNA-EGFRsiRNA-PSMA aptamer (PSEP) is about 59 Kd, which is much larger than current PSMA aptamer-siRNA chimeras[34,60] (around 29 Kd). To increase the in vivo circulation half-life, 20 Kd PEG has been added to the chimera in the previous study34 and proven to be effective. Chimera with a bivalent aptamer and dual siRNAs offers increased circulating half-life and reduced renal excretion.

In one embodiment, the RNA chimera incorporates 2' F into entire RNA chimera by T7 RNA polymerase-driven transcription. Previous reported aptamer-siRNA chimeras contain one strand unmodified siRNA34,36. 2' F completely modified RNA offers more serum stability than partial modified chimeras. The efficacy in tumor targeting and gene knockdown of both EGFR and survivin was confirmed, and the profound reduction of tumor size and inhibition of tumor-associated blood vessels have been achieved, suggesting the efficacy of targeting on multiple proliferation pathways.

Tumor angiogenesis is regulated by multiple mechanisms. Among them, VEGF expressed by tumor cells has been shown to play an essential role. PSEP specifically targets tumor-associated vessels as suggested by the reduction of blood vessels. PSEP can significantly inhibit VEGF secretion from C4-2 cells. The data further demonstrated that the inhibition of VEGF by PSEP was at least partially due to the blockade of EGFR-HIF1α signaling, which has been shown to be capable of inducing VEGF expression. Indeed, PSEP significantly reduced EGFR and HIF1α at both cellular and tissue levels. The efficacy of PSEP on anti-angiogenesis will contribute to many vascularized tumors since PSMA expression is up-regulated on endothelial cells of tumor-associated neovasculature, but not on normal endothelia cells (Chang, et al., *Clin Cancer Res*, 5: 2674-2681 (1999); Chang, et al., *Cancer Res*, 59: 3192-3198 (1999)).

The data shows that two different siRNAs can be simultaneously delivered by a bivalent aptamer. Co-delivery of two siRNAs in one RNA chimera provides a new and efficient approach for combination therapy. Since the system is highly modular, our work can be applied to many targeting co-delivery design by using siRNA and aptamer. The data also demonstrated that repeated administration is well tolerated and did not elicit an innate immune response.

Small interfering RNA (siRNA) has great potential for sequence-specific silencing of any genes and has emerged as a promising new therapeutic paradigm for "undruggable" targets (Hannon, et al., *Nature*, 418: 244-251 (2002); Jensen, et al., *Sci Transl Med*, 5: 209ra152. doi: 10.1126/scitranslmed.3006839 (2013); Wu, et al., *Sci Transl Med*, 6: 240ps7, doi:10.1126/scitranslmed.3008362 (2014)). However, the use of siRNA as a therapeutic has been hampered by the difficulty of delivery (Whitehead, et al., *Nat Rev Drug Discov*, 8: 129-138 (2009)). Recently, aptamers (synthetic DNA/RNA ligands) have proven to be a promising platform for delivering siRNA into cells. Selected in a process known as SELEX (systematic evolution of ligands by exponential enrichment) (Ellington, et al., *Nature*, 346: 818-822 (1990); Tuerk, et al., *Science*, 249: 505-510 (1990)), aptamers can specifically bind to various targets including organics, peptides, proteins and cells (Zhou, et al., *Front Genet*, 3: 234, doi:10.3389/fgene.2012.00234 (2012)). Particularly, cell-based SELEX allows the selection of internalized aptamers, which can induce the intracellular delivery of cargo through receptor-mediated endocytosis (Zhou, et al., *J Vis Exp*, 52: e2954, doi: 10.3791/2954 (2011)). Aptamers have specific 3-dimentional structures for target binding with high affinity, which can be maintained in vivo. Aptamer-siRNA chimera (AsiC), employing only RNA molecules, is a new targeting therapeutic (Dassie, et al., *Ther Deliv*, 4: 1527-1546 (2013); Wang, et al., *Theranostics*, 5: 1456-1472 (2015)) and has shown the promise of minimizing off-target effects that are usually associated with small molecule drugs and immunogenicity of antibody-based therapeutic. As a single-component entity, AsiC also has advantages in ease of synthesis and high tissue penetrability. Importantly, AsiC-based drugs can utilize endogenous enzymes (e.g., dicer, argonaute) and enable cell type- and mRNA sequence-specific gene silencing, which can provide selective and effective inhibition of protein targets regardless their cellular localization. For examples, CD4 aptamer-tat/rev siRNA chimera has shown the efficacy in inhibition of HIV transmission (Neff, et al., Sci Transl Med, 3: 66ra6, doi: 10.1126/scitranslmed.3001581 (2011)), PSMA aptamer-PLK1siRNA enables the regression of prostate cancer (Dassie, et al., Nat Biotechnol, 27: 839-849 (2009)). CTLA4 aptamer-STAT3 siRNA inhibits tumor-associated Tregs and reduces tumor burden in multiple mouse tumor models (Herrmann, et al., J Clin Invest, 124: 2977-2987 (2014)). EpCAM aptamer-survivin siRNA enables reversal of doxorubicin resistance and prolongs survival in mice bearing chemoresistant tumors (Wang, et al., Theranostics, 5: 1456-1472 (2015)).

B. Aptamers

The bivalent siRNA chimeras contain two aptamers. The aptamers can specifically bind the same target, or in some embodiments, the aptamers can specifically bind to different targets. In a preferred embodiment, the aptamers bind to the same target, for example PSMA.

Aptamers are molecules that interact with a target molecule, preferably in a specific way. Typically aptamers are small nucleic acids ranging from 15-200 bases in length that fold into defined secondary and tertiary structures, such as stem-loops or G-quartets. Aptamers can bind to protein, cells, small organic, peptide. Aptamers can bind small molecules, such as ATP and theophiline, as well as large molecules, such as reverse transcriptase and thrombin. Aptamers can bind very tightly with $K_d$'s from the target molecule of less than $10^{-12}$M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a molecule such as a polypeptide, that the background molecule be a different polypeptide.

Aptamers include binding to PDGF, nucleolin, P-selectin, EpCAM, CD44, Mucin, AXL, transferrin receptor, ErbB2, VEGFR, HIV-1 Tat protein, HIV Nuceocapsid, integrin, Her3, IL-10, anti-NF-KB, Kanamycin A, catenin, ERK2, C-reactive protein, L-tryptophan, SARS Coronavirus, influenza B, thrombin Hemagglutinin, tumor necrosis factor-alpha, VEGF, streptavidin, Kit-129, HIV Reverse transcriptase, insulin, PSA, RNase H1, Swine influenza A virus, Human neutrophil elastase, anti-IgE, L-selectin, 4-1BB, Tenascin-C, Protein Kinase C, RBP4, Enterotoxin B, her2, Hepatocyte growth factor receptor, Hepatitis C, Fibrogen, HGF, IgG, EGFR, survivin, Osteopontin, P-selectin, neurotrophin receptor, interferon-γ, Human matrix metalloprotease 9, Keratinocyte growth factor, MCP-1, von-Willebrand factor, Plasminogen activator inhibitor-1, OX40, CD4, CD3, CD8, Tenascin-C.

III. Targeted Cell Surface Proteins

The aptamers in the bivalent siRNA chimeras can specifically bind to a cell surface protein or a protein or peptide secreted into the microenvironment of cell to be treated, for example a cancer cell, tumor cell, or virally infected cell. In some embodiments, the protein or peptide that is specifically recognized by the aptamers of the bivalent siRNA chimera can be cell surface proteins involved in signal transduction, tumor specific antigens, tumor neovasculature antigens, viral proteins or viral peptides displayed in the surface of cells, cytokines, and cytokine receptors. These targeted proteins or peptides may be substances produced by a cell or may be substances which accumulate at a cell microenvironment site, or on cell surfaces.

In one embodiment, the aptamers of the bivalent siRNA chimeras specifically bind to prostate-specific membrane antigen (PSMA).

A. Tumor Specific Antigens

The disclosed aptamers may be specific to or selective for a variety of cell surface or disease-associated antigens. In certain embodiments, such as treating tumors, the aptamers of the disclosed compositions specifically bind tumor-associated antigens. These antigenic markers may be substances produced by a tumor or may be substances which accumulate at a tumor site, or on tumor cell surfaces.

In some embodiments, the targeting domains bind to antigens, ligands or receptors that are specific to tumor cells or tumor-associated neovasculature, or are upregulated in tumor cells or tumor-associated neovasculature compared to normal tissue.

1. Oncogenes

Tumor-associated antigens that are targeted by the disclosed compositions may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melanoma associated antigens, etc.).

Genes that encode cellular tumor associated antigens include cellular oncogenes and proto-oncogenes that are aberrantly expressed. In general, cellular oncogenes encode products that are directly relevant to the transformation of the cell, and because of this, these antigens are particularly preferred targets for immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

Exemplary oncogenes that can be targeted to direct the disclosed compositions to tumors, tumor cells, or tumor microenvironments include, but are not limited to ABL1, ABL2, AKT1, AKT2, ATF1, BCL11A, BCL2, BCL3, BCL6, BCR, BRAF, CARD11, CBLB, CBLC, CCND1, CCND2, CCND3, CDX2, CTNNB1, DDB2, DDIT3, DDX6, DEK, EGFR, ELK4, ERBB2, ETV4, ETV6, EVI1, EWSR1, FEV, FGFR1, FGFR1OP, FGFR2, FUS, GOLGA5, GOPC, HMGA1, HMGA2, HRAS, IRF4, JUN, KIT, KRAS, LCK, LMO2, MAF, MAFB, MAML2, MDM2, MET, MITF, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCL1A, TET2, TFG, MLL, TLX1, TPR, and USP6.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. 1 Med.*, 309:883 (1983); Lloyd, et al., *Int. J. Canc.*, 71:842 (1997). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.*, 36:755 (1997); Sarandakou, et al., *Eur. J. Gynaecol. Oncol.*, 19:73 (1998); Meier, et al., *Anticancer Res.*, 17(4B):2945 (1997); Kudoh, et al., *Gynecol. Obstet. Invest.*, 47:52 (1999)). Elevated serum CA125 may also accompany neuroblastoma (e.g., Hirokawa, et al., *Surg. Today*, 28:349 (1998), while elevated CEA and SCC, among others, may accompany colorectal cancer (Gebauer, et al., *Anticancer Res.*, 17(4B):2939 (1997)).

The tumor associated antigen, mesothelin, defined by reactivity with monoclonal antibody K-1, is present on a majority of squamous cell carcinomas including epithelial ovarian, cervical, and esophageal tumors, and on mesotheliomas. Using MAb K-1, mesothelin is detectable only as a cell-associated tumor marker and has not been found in soluble form in serum from ovarian cancer patients, or in medium conditioned by OVCAR-3 cells. Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies.

A tumor antigen may include a cell surface molecule. Tumor antigens of known structure and having a known or described function, include the following cell surface receptors: HER1 (GenBank Accession No. U48722), HER2 (GenBank Acc. Nos. X03363 and M17730), HER3 (GenBank Acc. Nos. U29339 and M34309), HER4 (GenBank Acc. Nos. L07868 and T64105), epidermal growth factor receptor (EGFR) (GenBank Acc. Nos. U48722, and KO3193), vascular endothelial cell growth factor (GenBank No. M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043), insulin-like growth factor-II (GenBank Acc. Nos. X03562, X00910, M17863 and M17862), transferrin receptor (Trowbridge and Omary, *Proc. Nat. Acad. USA*, 78:3039 (1981); GenBank Acc. Nos. X01060 and M11507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., *Proc. Nat. Acad. Sci. USA*, 86:7159 (1989); GenBank Acc. Nos. M65132 and M64928) NY-ESO-1 (GenBank Acc. Nos. AJ003149 and U87459), NA 17-A, Melan-A/MART-1 GenBank Acc. Nos. U06654 and U06452), tyrosinase (GenBank Acc. No. M26729), Gp-100 (GenBank Acc. No. S73003), MAGE (GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. No. U19180), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA; GenBank Acc. Nos. M59710, M59255 and M29540), and PyLT (GenBank Acc. Nos. J02289 and J02038); p97 (melanotransferrin).

Additional tumor associated antigens include prostate surface antigen (PSA); β-human chorionic gonadotropin (β-HCG); glycosyltransferase β-1,4-N-acetylgalactosaminyltransferases (GalNAc); NUC18; melanoma antigen gp75 (GenBank Accession No. X51455); human cytokeratin 8; high molecular weight melanoma antigen.

Tumor antigens of interest include antigens regarded in the art as "cancer/testis" (CT) antigens that are immunogenic in subjects having a malignant condition. CT antigens include at least 19 different families of antigens that contain one or more members and that are capable of inducing an immune response, including but not limited to MAGEA (CT1); BAGE (CT2); MAGEB (CT3); GAGE (CT4); SSX (CT5); NY-ESO-1 (CT6); MAGEC (CT7); SYCP1 (C8); SPANXB1 (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but not limited to, alpha-actinin-4, Bcr-Abl fusion protein, Casp-8, beta-catenin, cdc27, cdk4, cdkn2a, coa-1, dek- can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4, 5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art and are suitable for targeting by the disclosed fusion proteins.

2. Tumor Neovasculature Antigens

The targeted antigen may be specific to tumor neovasculature or may be expressed at a higher level in tumor neovasculature when compared to normal vasculature. Exemplary antigens that are over-expressed by tumor-associated neovasculature as compared to normal vasculature include, but are not limited to, VEGF/KDR, Tie2, vascular cell adhesion molecule (VCAM), endoglin and $\alpha_5\beta_3$ integrin/vitronectin. Other antigens that are over-expressed by tumor-associated neovasculature as compared to normal vasculature are known to those of skill in the art and are suitable for targeting by the disclosed fusion proteins.

B. Chemokine or Chemokine Receptors

In another embodiment, the aptamer on the composition specifically binds to a chemokine or a chemokine receptor. Chemokines are soluble, small molecular weight (8-14 kDa) proteins that bind to their cognate G-protein coupled receptors (GPCRs) to elicit a cellular response, usually directional migration or chemotaxis. Tumor cells secrete and respond to chemokines, which facilitate growth that is achieved by increased endothelial cell recruitment and angiogenesis, subversion of immunological surveillance and maneuvering of the tumoral leukocyte profile to skew it such that the chemokine release enables the tumor growth and metastasis to distant sites. Thus, chemokines are important for tumor progression.

Based on the positioning of the conserved two N-terminal cysteine residues of the chemokines, they are classified into four groups namely CXC, CC, CX3C and C chemokines. The CXC chemokines can be further classified into ELR+ and ELR– chemokines based on the presence or absence of the motif 'glu-leu-arg (ELR motif)' preceding the CXC sequence. The CXC chemokines bind to and activate their cognate chemokine receptors on neutrophils, lymphocytes, endothelial and epithelial cells. The CC chemokines act on several subsets of dendritic cells, lymphocytes, macrophages, eosinophils, natural killer cells but do not stimulate neutrophils as they lack CC chemokine receptors except murine neutrophils. There are approximately 50 chemokines and only 20 chemokine receptors, thus there is considerable redundancy in this system of ligand/receptor interaction.

Chemokines elaborated from the tumor and the stromal cells bind to the chemokine receptors present on the tumor and the stromal cells. The autocrine loop of the tumor cells and the paracrine stimulatory loop between the tumor and the stromal cells facilitate the progression of the tumor. Notably, CXCR2, CXCR4, CCR2 and CCR7 play major roles in tumorigenesis and metastasis. CXCR2 plays a vital role in angiogenesis and CCR2 plays a role in the recruitment of macrophages into the tumor microenvironment. CCR7 is involved in metastasis of the tumor cells into the sentinel lymph nodes as the lymph nodes have the ligand for CCR7, CCL21. CXCR4 is mainly involved in the metastatic spread of a wide variety of tumors.

In one embodiment, tumor or tumor-associated neovasculature targeting domains are ligands that bind to cell surface antigens or receptors that are specifically expressed on tumor cells or tumor-associated neovasculature or are overexpressed on tumor cells or tumor-associated neovasculature as compared to normal tissue. Tumors also secrete a large number of ligands into the tumor microenvironment that affect tumor growth and development. Receptors that bind to ligands secreted by tumors, including, but not limited to growth factors, cytokines and chemokines, including the chemokines provided above, are suitable for use in the disclosed fusion proteins. Ligands secreted by tumors can be targeted using soluble fragments of receptors that bind to the secreted ligands. Soluble receptor fragments are fragments polypeptides that may be shed, secreted or otherwise extracted from the producing cells and include the entire extracellular domain, or fragments thereof.

In another embodiment the aptamers of the disclosed compositions specifically bind to target antigens selected from the group consisting of carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1α, AFP, PSMA, CEACAM5, CEACAM6, c-met, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, C5, PLAGL2, and an oncogene product. A particularly preferred target antigen is CEACAM5 (CEA).

C. Viral Antigens

In some embodiments, the protein that is bound by the aptamer is a viral protein selected from the group consisting of a pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, and hepatitis E virus.

D. Genes to be Down-Regulated

The disclosed bivalent siRNA chimeras contain two or more siRNAs that specifically inhibit or down-regulated expression of two or more different genes. In some embodiments, the two or more different genes are oncogenes. In a preferred embodiment, at least one siRNA inhibits or reduces the expression of survivin.

1. Oncogenes

Exemplary oncogenes or proto-oncogenes that can be inhibited by the siRNA include, but are not limited to the oncogenes and proto-oncogenes discussed above is Section II.A.1. Representative oncogenes that can be down-regulated by the siRNA in the chimeras include, for example ABL1, ABL2, AKT1, AKT2, ATF1, BCL11A, BCL2, BCL3, BCL6, BCR, BRAF, CARD11, CBLB, CBLC, CCND1, CCND2, CCND3, CDX2, CTNNB1, DDB2, DDIT3, DDX6, DEK, EGFR, ELK4, ERBB2, ETV4, ETV6, EVI1, EWSR1, FEV, FGFR1, FGFR1OP, FGFR2, FUS, GOLGA5, GOPC, HMGA1, HMGA2, HRAS, IRF4, JUN, KIT, KRAS, LCK, LMO2, MAF, MAFB, MAML2, MDM2, MET, MITF, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCL1A, TET2, TFG, MLL, TLX1, TPR, and USP6.

Sequence information for these oncogenes are known in the art, and one of skill in the art could readily make siRNA constructs to specifically inhibit oncogene expression.

The EGFR and survivin pathways represent two independent while interacting survival mechanisms in many cancer cells. As nodal proteins, EGFR and survivin intersect multiple signaling networks, therefore targeting both molecules might lead to global pathway inhibition regardless of tumor heterogeneity. Interestingly, it also has been shown that tumor resistant to EGFR inhibitors may switch to the survivin network for survival and recurrence (Altieri, et al., *Nature Reviews Cancer*, 8: 61-70 (2008)). Therefore, one embodiment provides co-targeting EGFR and survivin to more effectively inhibit multiple oncogenic signals. Current combination of kinase inhibitors has the overlapping toxicities, while monoclonal antibodies cannot access and block intracellular signaling molecules (e.g., survivin) (Pecot, et al., *Nat Rev Cancer*, 11: 59-67 (2011)), and are usually associated with high costs, complex production and immunogenicity (Harding, et al., MAbs, 2: 256-265 (2010)).

2. Virus Expression to be Inhibited.

Genes encoding viruses or virus components can be targeted for siRNA inhibition using the bivalent siRNA chimeras. Exemplary viruses to be targeted for siRNA inhibition include, but are not limited to pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, and hepatitis E virus.

Sequence information for the genes of these viruses are known in the art, and one of skill in the art could readily make siRNA constructs to specifically inhibit viral gene expression.

IV. siRNA

Figure 1B:
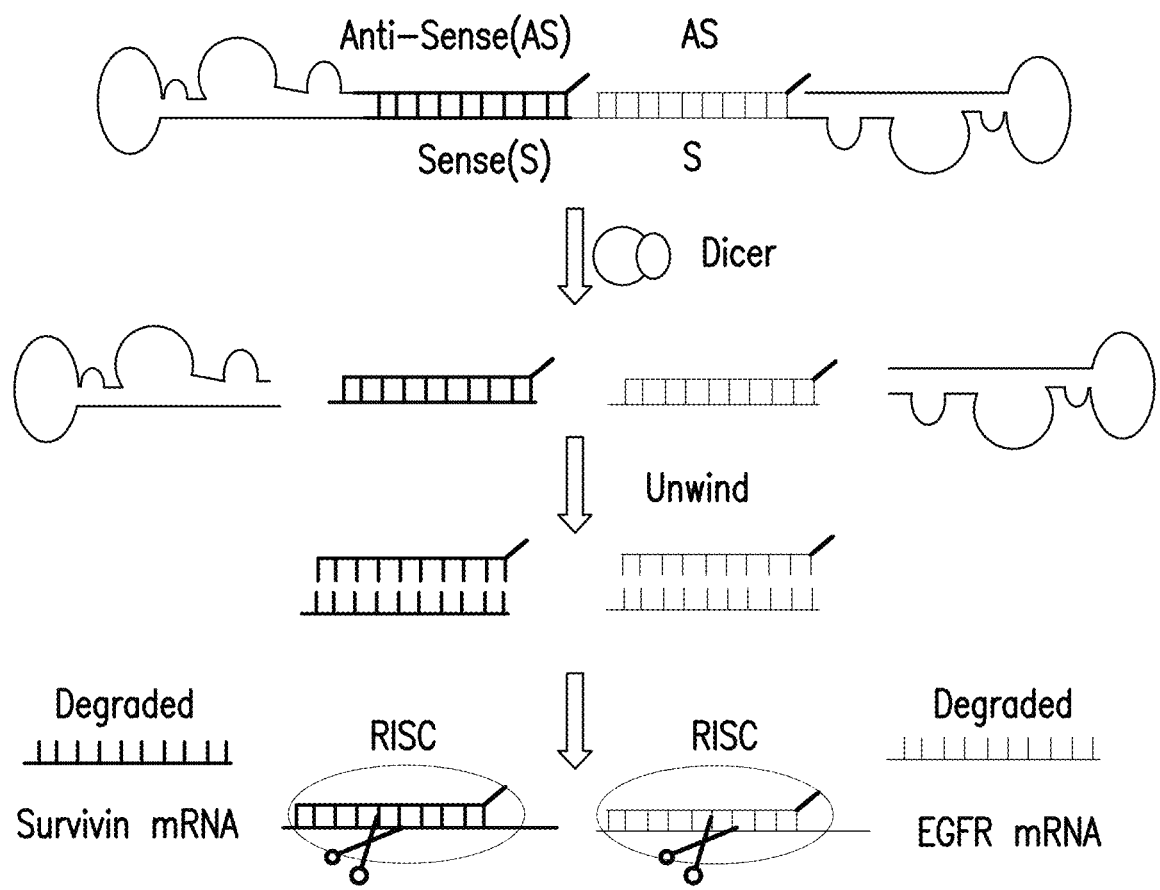

The bivalent siRNA chimeras contain siRNA that specifically inhibit expression of two or more genes. The siRNA in the chimera is processed using cellular siRNA machinery to produce siRNA in active form (FIG. 1B).

Gene expression can be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

V. Methods of Use

The disclosed bivalent siRNA chimeras can be used to down-regulate specific genes in targeted cells. In some embodiments, the chimeras are used to down-regulated two or more genes in a targeted cell through siRNA inhibition. The aptamers in the chimeras can be designed to target a protein or peptide that is expressed by the cell.

A. Cancer

In one embodiment, the bivalent siRNA chimeras are administered to a subject having or suspected of having cancer in an amount effective to inhibit expression of two or more genes in the cancer survival pathway. For example, the divalent siRNA chimera can have two aptamers that specifically bind to a cancer antigen or a tumor specific antigen.

A preferred tumor specific antigen is PSMA. The genes to be down-regulated in the cancer or tumor cell are typically oncogenes or proto-oncogenes, for example survivin and EGFR. In another embodiment, survivin is down-regulated and an oncogene selected from the group consisting of ABL1, ABL2, AKT1, AKT2, ATF1, BCL11A, BCL2, BCL3, BCL6, BCR, BRAF, CARD11, CBLB, CBLC, CCND1, CCND2, CCND3, CDX2, CTNNB1, DDB2, DDIT3, DDX6, DEK, ELK4, ERBB2, ETV4, ETV6, EVI1, EWSR1, FEV, FGFR1, FGFR1OP, FGFR2, FUS, GOLGA5, GOPC, HMGA1, HMGA2, HRAS, IRF4, JUN, KIT, KRAS, LCK, LMO2, MAF, MAFB, MAML2, MDM2, MET, MITF, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCL1A, TET2, TFG, MLL, TLX1, TPR, and USP6 is also down-regulated.

Thus, methods for treating prostate cancer are provided. Other cancers that can be treated include, but are not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer such as but not limited to papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers including, but not limited to, Cushing's disease, prolactin-secreting tumor, acromegaly, and diabetes insipius; eye cancers including, but not limited to, ocular melanoma such as iris melanoma, choroidal melanoma, and ciliary body melanoma, and retinoblastoma; vaginal cancers, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including, but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or ureter); Wilms' tumor; bladder cancers including, but not limited to, transitional cell carcinoma, squamous cell cancer, adenocarcinoma, carcinosarcoma. Cancers that can be prevented, treated or otherwise diminished by the MDNPs include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, papillary adenocarcinomas, and gastric cancer.

B. Tumor Burden

Another embodiment provides a method for reducing the tumor burden of a subject by administering an effective amount of a bivalent siRNA chimera that specifically binds a tumor specific antigen produced by the tumor and is processed by cellular iRNA machinery to produce two or more siRNAs that inhibit the expression of at least two genes in the tumor to promote apoptosis of tumor cells.

C. Viral Infections

Another embodiment provides a method for treating a viral infection in a subject in need thereof by administering an effective amount of bivalent siRNA chimeras that contain aptamers that specifically bind to proteins on the virus expressed on the surface of virally infected cells and wherein the chimera is internalized by a virally infected celled and processed to produce two or more siRNAs that inhibit viral genes.

Exemplary viruses that can be treated include, but are not limited to pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, and hepatitis E virus.

D. Co-Therapies

The divalent siRNA chimeras can be used in combination or alternation with a second therapeutic.

1. Cancer Co-Therapies

Non-limiting examples of one or more other therapies that can be used in combination with the bivalent siRNA chimeras include immunomodulatory agents, such as but not limited to, chemotherapeutic agents and non-chemotherapeutic immunomodulatory agents. Non-limiting examples of chemotherapeutic agents include cyclophosphamide, methotrexate, cyclosporin A, leflunomide, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan. Examples of non-chemotherapeutic immunomodulatory agents include, but are not limited to, anti-T cell receptor antibodies (e.g., anti-CD4 antibodies (e.g., cM-T412 (Boeringer), IDEC-CE9.1 ☐ (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies (e.g., MEDI-507 (MedImmune, Inc., International Publication Nos. WO 02/098370 and WO 02/069904), anti-CD11a antibodies (e.g., Xanelim (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-alpha antibodies, anti-IL-1alpha antibodies, anti-IL-6 antibodies, anti-IL-8 antibodies (e.g., ABX-TL-8 (Abgenix)), anti-IL-12 antibodies and anti-IL-23 antibodies)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-alpha receptor or a fragment thereof, the extracellular domain of an IL-1 alpha receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-12, IL-15, IL-23, INF-alpha, INF-beta, interferon (IFN)-alpha, IFN-beta, IFN-gamma, and GM-CSF); and anti-cytokine antibodies (e.g., anti-IL-2 antibodies, anti-IL-4 antibodies, anti-IL-6 antibodies, anti-IL-10 antibodies, anti-IL-12 antibodies, anti-IL-15 antibodies, anti-TNF-alpha antibodies, and anti-IFN-gamma antibodies), and antibodies that immunospecifically bind to tumor-associated antigens (e.g., Herceptin®). In certain embodiments, an immunomodulatory agent is an immunomodulatory agent other than a chemotherapeutic agent. In other embodiments an immunomodulatory agent is an immunomodulatory agent other than a cytokine or hemapoietic such as IL-1, IL-2, IL-4, IL-12, IL-15, TNF, IFN-alpha, IFN-beta, IFN-gamma, M-CSF, G-CSF, IL-3 or erythropoietin. In yet other embodiments, an immunomodulatory agent is an agent other than a chemotherapeutic agent and a cytokine or hemapoietic factor.

Non-limiting examples of anti-cancer agents that can be used as therapies in combination with the bivalent siRNA chimeras, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimus tine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidasc; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stern cell inhibitor; stem-cell division inhibitors; stipiamide; stromelysin inhibitors; sulfinosinc; superactivc vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stern cell factor; translation inhibitors; tretinoin; triacetyluridine; triciribinc; trimetrexate; triptorelin; tropisetron; turosteridc; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanotcrone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In specific embodiments, the anti-cancer agent is not a chemotherapeutic agent.

2. Antiviral Co-Therapies

Antiviral agents that can be used in combination with bivalent siRNA chimeras include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide.

Additional, non-limiting examples of antiviral agents for use in combination with bivalent siRNA chimeras include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; avridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oscltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

3. Genetic Disorder Co-Therapies

Genetic disorders including: Down's Syndrome, muscular dystrophy, Huntington's Disease. Asthma, heart disease, diabetes, obesity, hypertension, X-linked dominant genetic diseases, and autosomal dominant genetic diseases can be treated using the disclosed bivalent siRNA chimeras. The genes known to be involved in the genetic disease or syndrome can be targeted for down-regulation using the disclosed bivalent siRNA chimera platform.

E. Administration and Formulations

The disclosed bivalent siRNA chimeras can be formulated as pharmaceutical compositions for parenteral administration. The formulations can contain one or more pharmaceutically acceptable excipients.

EXAMPLES

Example 1: Engineering of a Bivalent Aptamer-Dual siRNA Chimera. PSMA Aptamer-Survivin siRNA-EGFR Materials and Methods Chemicals and Cell Culture.

Vendors for specific chemicals are listed below. Cell culture products were purchased from Invitrogen (Carlsbad, Calif.). Antibodies were from Cell Signaling Technology (Danvers, Mass.) except for anti-CD31 from Abcam (Cambridge, Mass.) and PSMA from BioLegend (San Diego, Calif.). Single stranded DNAs were synthesized by Integrated DNA Technologies (IDT, Coralville, Iowa). TranscriptAid T7 High Yield Transcription Kits and Cy3-CTP were purchased from Thermo Fisher Scientific. PCR reagents were from Sigma-Aldrich (St Louis, Mo.). LysoTracker Green DND-26 and Alexa Fluor 488 Annexin V/Dead Cell Apoptosis kits were from Invitrogen. ELISA kits for detection of VEGF-A, IFNα and IL-6 were obtained from RayBiotech (Norcross, Ga.). TUNEL assay kit was purchased from R&D systems (Minneapolis, Minn.). Cell lines including PC3, BXPC3 and T-24 were purchased from the American Type Culture Collection (ATCC, Manassas, Va.) and C4-2 cells were from Dr. Daqing Wu's Laboratory. SMARTer RACE 5'/3' kits were purchased from Clontech (Mountain View, Calif.). ELISA kit for mouse IFN alpha was obtained from R&D systems. GeneSolution siRNA specific to PSMA was ordered from Qiagen (Germantown, Md.). Human serum (Normal Pool) was obtained from Thermo Fisher Scientific.

Aptamer-siRNA Chimera Synthesis.

The ssDNA templates and primers were synthesized from IDT. For PSEP (PSMA aptamer-surivin siRNA-EGFR siRNA-PSMA aptamer), three RNA molecules (RNA1, RNA2 and RNA3) were constructed individually:

```
RNA 1: PSMA aptamer- survivin antisense siRNA:
                                     (SEQ ID NO: 1)
5'-GGGAGGACGAUGCGGAUCAGCCAUGUUUACGUCACUCCUAAAA

UGUAGAGAUGCGGUGGUCCUU-3'.

RNA1 PCR template:
                                     (SEQ ID NO: 2)
5'-
GGGAGGACGATGCGGATCAGCCATGTTTACGTCACTCCTAAAATGT

AGAG ATGCGGTGGTCCTT-3'.

RNA1 5' primer:
                                     (SEQ ID NO: 3)
5'-TAATACGACTCACTATAGGGAGGACGATGCGG-3'
(F1).
The forward primer contains T7 RNA polymerase
promoter site (bolded).

(SEQ ID NO: 4)
RNA1 3' primer:
5'-AAGGACCACCGCATCTCTACATTTTAGGAGTGAC

GTAAAC-3' (R1).

RNA2: PSMA aptamer-EGFR sense siRNA-survivin
sense siRNA:
                                     (SEQ ID NO: 5)
5'-GGGAGGACGAUGCGGAUCAGCCAUGUUUACGUCACUCCUAAA

ACCUUAGCAGUCUUAUCUAAUUUUGGACCACCGCAUCUCUACAU

U-3'.

RNA2 PCR template:
                                     (SEQ ID NO: 6)
5'-GGGAGGACGATGCGGATCAGCCATGTTT

ACGTCACTCCTAAAACCTTAGCAGTCTTATCTAATTTTGGAC

CACCGCATCTCTACATT-3'.

RNA2 5' primer:
F1

RNA2 3' primer:
                                     (SEQ ID NO: 7)
5'-AATGTAGAGATGCGGTGGTCCAAAATTAGA-3' (R2).

RNA3: EGFR anti-sense strand:
                                     (SEQ ID NO: 8)
5'-UUAGAUAAGACUGCUAAGGCA-3'.

RNA3 PCR template:
                                     (SEQ ID NO: 9)
5'-TAATACGACTCACTATATTAGATAAGA

CTGCTAAGGCA-3'.
```

```
RNA3 5' primer:
                                    (SEQ ID NO: 10)
5'-TAATACGACTCACTA-3' (F2).

RNA3 3' primer:
                                    (SEQ ID NO: 11)
5'-TGCCTTAGCAGTCTT-3' (R3).
```

Three RNAs were generated by in vitro transcription with PCR products as templates. The PCR products were sequenced or put into T-A cloning pCR2.1 vector (Invitrogen) and sequenced. Transcription was performed with TranscriptAid T7 High Yield Transcription Kit following manufacture's instruction. 2' F-modified pyrimidines (TriLink, San Diego, Calif.) were incorporated into RNA to replace CTP and UTP. In some cases, the chimeras were synthesized with a Cy3-labeled CTP. The transcribed RNAs were purified with phenol/chloroform/isoamyl alcohol (25:24:1) (Sigma-Aldrich), precipitated with isopropanol (Sigma-Aldrich) followed by cold 70% ethanol wash. The RNA pellets were dissolved in nuclease free water (IDT). The purification procedures were used for all transcribed RNAs. Three RNAs were mixed at molar ratio 1:1:1 and annealed to form one entity by heated at 94° C. for 3 min followed by slowly cooling to room temperature within 1 h.

```
For PSMAapt-CON (PSMA aptamer-scrambled siRNA):
                                    (SEQ ID NO: 12)
5'-GGGAGGACGAUGCGGAUCAGCCAUGUUUACGUCAC

UCCUAAAAAACAGUCGCGUUUGCGACUGG-3'.

Two RNAs (RNA4 and RNA5) were synthesized
individually.
RNA4: PSMA aptamer- scrambled anti-sense siRNA:
                                    (SEQ ID NO: 13)
5'-GGGAGGACGATGCGGATCAGCCATGTTTACGTCACTCCTA

AAACCAGTCGCAAAGCGCUGACAC-3'.

RNA4 PCR template:
                                    (SEQ ID NO: 14)
5'-GGG AGGACGATGCGGATCAGCCATGTTTA

CGTCACTCCTAAAA-3'.

RNA4 5' primer:
F1,

RNA4 3' primer:
                                    (SEQ ID NO: 15)
5'-TTGTCAGCGCTTTGCGACTGGTTTTAGGAGTGACGTAAAC-3'
(R4).

RNA 5: Scrambled siRNA sense strand:
                                    (SEQ ID NO: 16)
5'-GTGTCAGCGCUUUGCGACUGG-3'.

RNA5 PCR template:
                                    (SEQ ID NO: 17)
5'-TAATACGACTCACTATAGTGTCAGCGCTTTGCGACTGG-3'.

RNA5 5' primer:
                                    (SEQ ID NO: 18)
5'-TAATACGACTCACTA-3' (F3).

RNA5 3' primer:
                                    (SEQ ID NO: 19)
5'-CCAGTCGCAAAGCGCT-3' (R5).
```

RNA4 and RNA5 were generated with transcription and annealed at molar ratio of 1:1 to generate PSMAapt-CON chimera.
For PSP (PSMA aptamer-survivin siRNA-PSMA aptamer). Two RNAs (RNA1 and RNA6) are individually constructed and annealed to form PSP. RNA1 (PSMA aptamer-survivin antisense siRNA) was described above.

```
RNA 6: PSMA aptamer- survivin sense siRNA:
                                    (SEQ ID NO: 20)
5' GGGAGGACGAUGCGGAUCAGCCAUGUUUACGUCA

CUCCUUUGGACCACCGCAUCUCUACAUU-3'.

RNA6 PCR template:
                                    (SEQ ID NO: 21)
5' -GGGAGGACGATGCGGATCAGCCATGTTTACGTCACTCCTTTGG

ACCACCGCATCTCTACATT-3'.

RNA6 5' primer: F1

RNA6 3' primer:
                                    (SEQ ID NO: 22)
5' -AATGTAGAGATGCGGTGGTCCAAAGGAGTGACGTAAACATG-3'

(R6).
```

For PEP (PSMA aptamer-EGFR siRNA-PSMA aptamer), two RNAs (RNA7 and RNA8) were individually constructed and annealed to form PEP.

```
RNA 7: PSMA aptamer-EGFR antisense siRNA:
                                    (SEQ ID NO: 23)
5'-GGGAGGACGAUGCGGAUCAGCCAUGUUUAC

GUCACUCCUAAAAUU AGAUAAGACUGCUAAGGCA-3'.

RNA7 PCR template:
                                    (SEQ ID NO: 24)
5'-TAATACGACTCACTATAGGGAGGACGATGCGGATCAGCCATGT

TTACGTCACTCCTAAAATTAGATAAGACTGCTAAGGCA-3'.

RNA7 5' primer:
F1.

RNA7 3' primer:
                                    (SEQ ID NO: 25)
5'-TGCCTTAGCAGTCTTATCTAATTTTAGGAGTGACGTAAAC-3'
(R7).

RNA8: PSMA aptamer-EGFR sense siRNA:
                                    (SEQ ID NO: 26)
5'-GGGAGGACGAUGCGG AUCAGCCAUGUUU

ACGUCACGUCCUCCUUAGCAGUCUUA UCUAAUU-3'.

RNA8 PCR template:
                                    (SEQ ID NO: 27)
5'-GGGAGGACGATGCGGATCAGCCATGTTTACG

TCACGTCCTCCTTAGCAGTCTTATCTAATT-3'.

RNA8 5' primer:
F1.

RNA8 3' primer:
                                    (SEQ ID NO: 28)
5'-AATTAGATAAGACTGCTAAGGAGGACGTGACGT-3'
(R8).
```

For MSEM:
MG aptamer (specific to Malachite Green)-survivin siRNA-EGFR siRNA-MG aptamer, three RNA molecules (RNA3, RNA9 and RNA10) were individually constructed and annealed together to form MSEM. RNA3 (EGFR antisense strand) was described above.

RNA9:
MG aptamer-EGFR sense siRNA-survivn sense siRNA:
(SEQ ID NO: 29)
5'-GGAUCCCGACUGGCGAGAGCCAGGUACGAAUGGAUCCAAAAACCU

UAGCAGUCUUAUCUAAUUUUGGACCACCGCAUCUCUACAUU-3'.

RNA9 PCR template:
(SEQ ID NO: 30)
5'-GGATCCCGACTGGCGAGAGCCAGGTAACG

AATGGATCCAAAAACCTTAGCAGTCTTATCTAATTTTGGACCA

CCGCATCTCTACATT-3'.

RNA9 5' primer:
(SEQ ID NO: 31)
5'-TAATACGACTCACTATAGGATCCCGACTGGCGA

GAGCCAGG-3' (F4).

RNA9 3' primer:
(SEQ ID NO: 32)
5'-AATGTAGAGATGCGGTGGTCCAAAATTAGA-3'
(R9)

RNA10: MG aptamer-survivin antisense siRNA:
(SEQ ID NO: 33)
5-GGAUCCCGACUGGCGAGAGCCAGGUAACGAA UGGAUCCUU

UUGUAGAGAUGCGGUGGUCCUU-3'.

RNA10 PCR template:
(SEQ ID NO: 34)
5'-GGATCCCGACTGGCGAGAGCCAGG

TAACGAATGGATCCTTTTGTAGAGATGCGGTGGTCCTT-3'.

RNA10 5' primer:
F4

RNA10 3' primer:
(SEQ ID NO: 35)
5'-AAGGACCACCGCATCTCTACAAAAGGATCCA-3'.
(R10)

For PSEM (PSMA aptamer-survivin siRNA-EGFR siRNA-MG aptamer), three RNAs (RNA9, RNA1 and RNA3) were annealed together at the molar ratio of 1:1:1.

In Vitro Dicer Assay.

PSEP (4 µg) was digested using human recombinant dicer enzyme (2 units) at 37° C. for either 6 h or 12 h following manufacturer's instructions (Genlantis, San Diego, Calif.). Reaction was quenched by adding dicer stop solution. The digestion pattern was analyzed on 3.5% agarose gel electrophoresis.

Statistical Analysis.

The results were expressed as a mean±SD. All Data were analyzed using two-tailed Student's t-test (Graph Pad Prism) by comparing with the control group, and $P<0.05$ was considered statistically significant.

Results

A bivalent aptamer siRNA chimera was designed to target two important oncogenes: EGFR and survivin, respectively. First, three individual RNA molecules were prepared respectively, two of them contain a 39-nt PSMA aptamer (A10-3.2) (Dassie, et al., Nat Biotechnol, 27: 839-849 (2009)) and one strand of siRNAs. Specifically, one RNA is composed of a PSMA aptamer and a survivin anti-sense strand, and another RNA is composed of a PSMA aptamer and two tandem sense strands of siRNAs specific to EGFR and survivin. Two aptamer-containing RNA molecules are synthesized by T7 RNA polymerase-driven transcription with DNA template from PCR products. The third RNA, EGFR anti-sense stand, is synthesized by transcription as well. To unite the three RNAs to one, two aptamer-containing RNA molecules and EGFR anti-sense strand are mixed at the molar ratio 1:1:1, heated to 95° C. for 3 min, and cooled down slowly to the room temperature within 1 h. By annealing, a chimera with a bivalent aptamer and dual siRNAs is formed (FIG. 1A). Survivin anti-sense and EGFR anti-sense strands with 2-nt overhang at the 3' end of siRNA where designed which can facilitate the siRNA-RISC (RNA-induced silencing complex) formation (Ma, et al., Nature, 429: 318-322 (2004)). To minimize nuclease-mediated degradation, 2' fluoro (F)-pyrimidines are incorporated into entire chimera via in vitro transcription. The inclusion of 2' F modification of all pyrimidines is expected to have improved serum stability of PSEP. To retain the flexibility and functionality of the aptamers and siRNAs, four "A"s were inserted between aptamer and siRNA, and four "U"s were inserted at the junction site of two siRNAs.

Figure 1C:
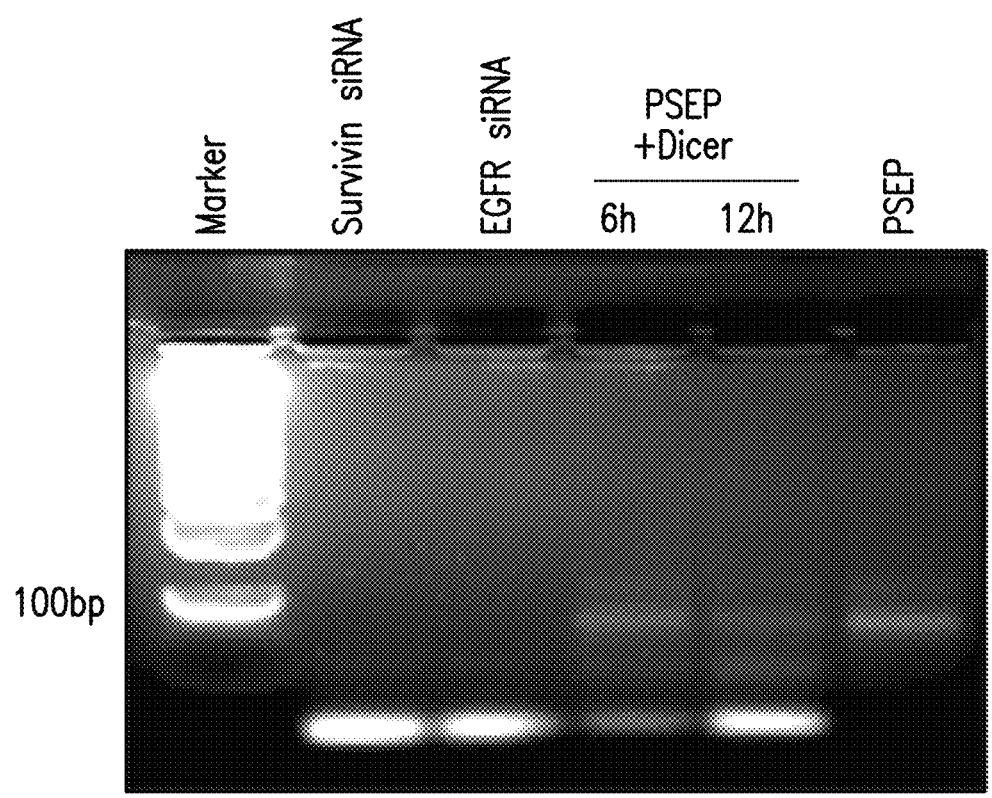

The mechanism of processing chimera is proposed and shown in FIG. 1B. PSEP chimera will enter to the cytoplasm and is processed by endonuclease dicer. Dicer will digest stem-loop containing PESP and produce two 21-nt siRNA duplex. After enzymatic unwinding siRNA duplex, anti-sense strand (guide strand) of siRNA will be selectively loaded into RISC complex, where Argonaute (Ago) protein family will mediate cleavage of mRNAs that are complementary to the siRNA guide strands. The sense strand (passenger) of siRNA will be degraded by endonucleases. To prove that PSEP can be effectively processed by dicer, we treated PSEP with human recombinant dicer for 6 h or 12 h. The digestion patterns were examined with 3.5% agarose electrophoresis. The gel images showed that the small RNAs were produced, with the same size as the free siRNAs against EGFR and survivin, suggesting PSEP can be processed by dicer (FIG. 1C).

Example 2: PSEP Serum Stability

Materials and Methods

Serum Stability Assay.

2' F-modified and unmodified PSEP (2 nmol) were incubated with final 50% human serum at 37° C. for 1-4 h. In another test, 2' F-modified PSEP (2 nmol) were incubated with 50% human serum for 24 h. RNA integrity was detected with denaturing 5% acrylamide/8 M urea gel electrophoresis63. PSEP intensity was measured with ImageJ (NIH).

Results

Figure 1D:
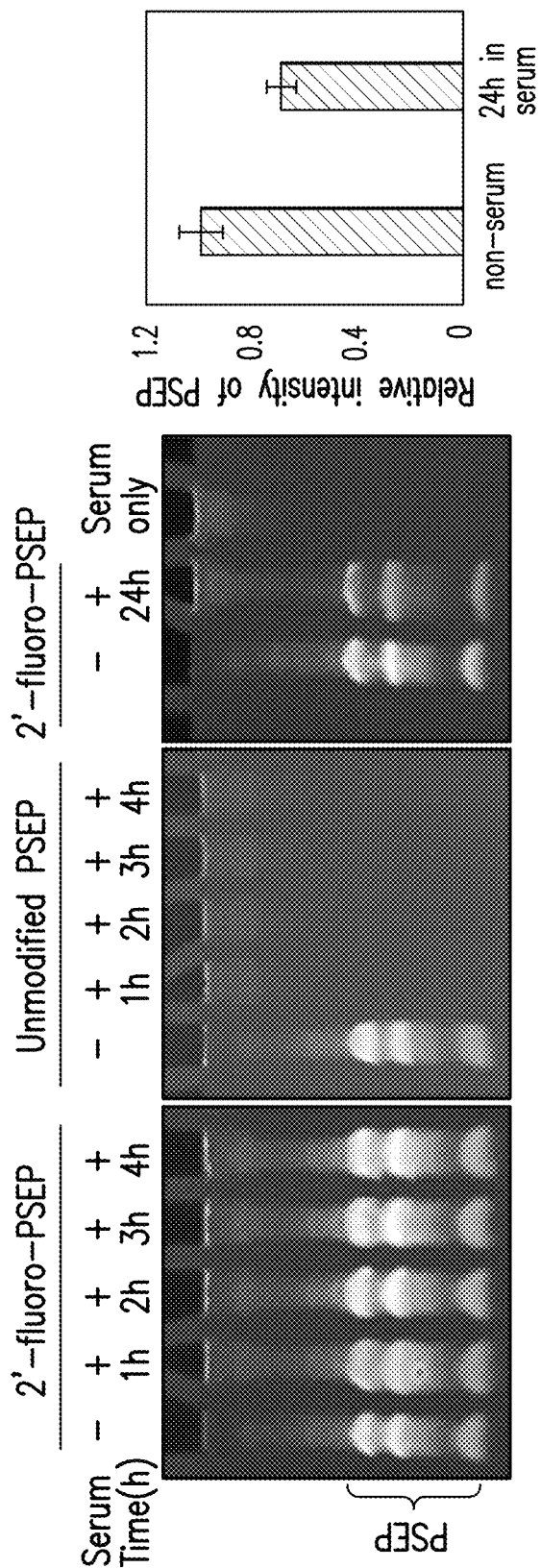

PSEP chimera was incubated in phosphate-buffered saline (PBS) containing 50% of fresh human serum for 1, 2, 3 and 4 h. Denaturing 5% acrylamide/8 M urea gel electrophoresis revealed that 2' F-modified PSEP did not show detectable degradation within 4 h; on the contrary, a degradation pattern was observed for unmodified PSEP in which no bands appeared as early as at 1 h. Over 60% of modified RNA kept the integrity (tight band) without degradation even after 24-h incubation (FIG. 1D). A similar result was also visualized by using fresh 50% mouse serum. In agreement with these results, other studies have demonstrated that chemical modification can significantly enhance the resistance of RNA to nuclease attack (Haringsma, et al., Nucleic Acids Res, 40: 4125-4136 (2012); Sioud, et al., Eur J Immunol, 36: 1222-1230 (2006)). In particular, replacing 2'-OH of RNA with 2'-amino or 2'-fluoro enhances the resistance to ribonucleases because ribonucleases select 2'-OH group for cleavage of phosphodiester bonds[49]. The results suggest that PSEP is stable in the serum.

Example 3: Comparison of Internalization

Materials and Methods

Evaluation of Binding and Internalization by Confocal Microscopy and Flow Cytometry.

C4-2 cells were seeded on 12 mm (diameter) cover-glass at a density of 5×104 cell/well for 24 h in RPMI 1640 supplemented with 5% fetal bovine serum. Cy3-labeled PSEP, PSEM, or MSEM (100 nM) was added into culture for 2 h at 37° C. At the same time LysoTracker™ Green DND-26 (80 nM) and yeast tRNA (300 µg/ml) was added to the culture medium for imaging. Images were captured using confocal laser scanning microscope (Zeiss LSM 510) and analyzed with Zeiss LSM image Browser Version 4.0. Quantification of Cy3 fluorescence intensity is through ImageJ (NIH). Quantitative flow cytometry was performed to detect internalized chimeras. C4-2 cells ($1\times10^5$/well) in 6-well culture plates were cultured for 24 h in RPMI 1640 supplemented with 5% fetal bovine serum. Cy3-labeled PSEP, PSEM, or MSEM (100 nM each) was added into culture for 2 h at 37° C. Yeast tRNA (300 µg/ml) was added to the medium during culture for blocking nonspecific binding. Next, cells were washed with DPBS plus 0.5 M NaCl to remove surface bound RNAs34. The internalized chimeras were detected with BD FACSCalibur flow cytometry.

Results

Figure 1E:
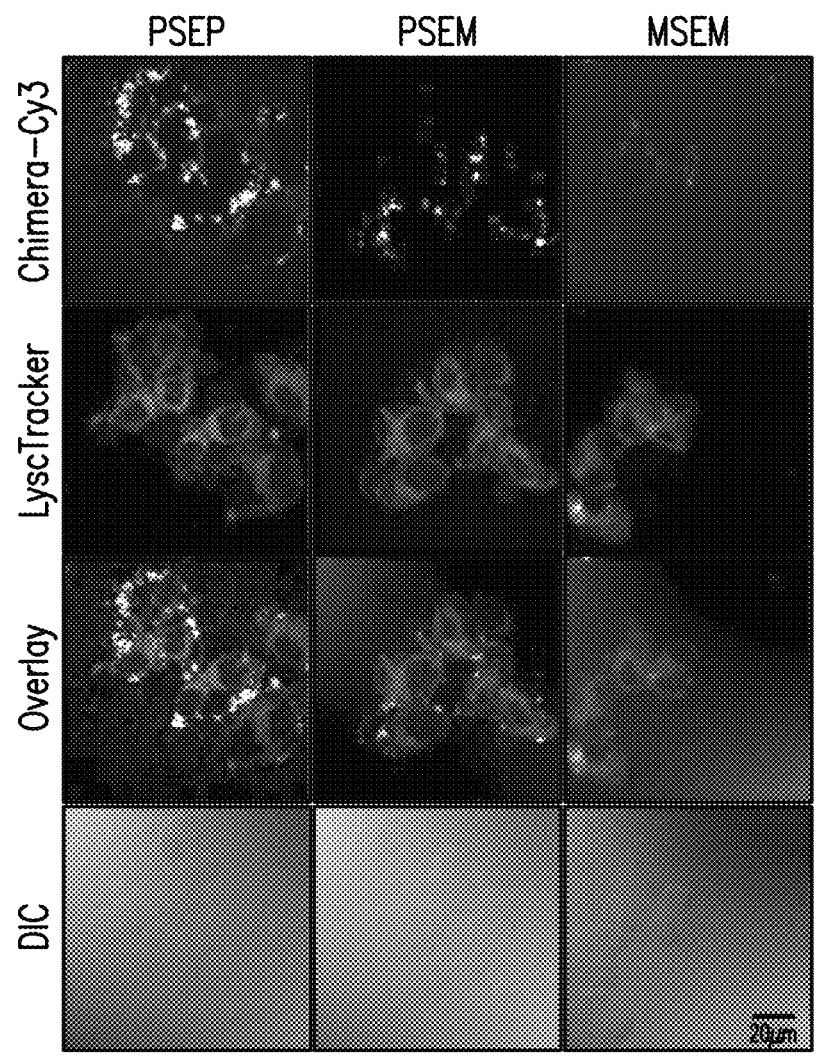
Figure 1F:
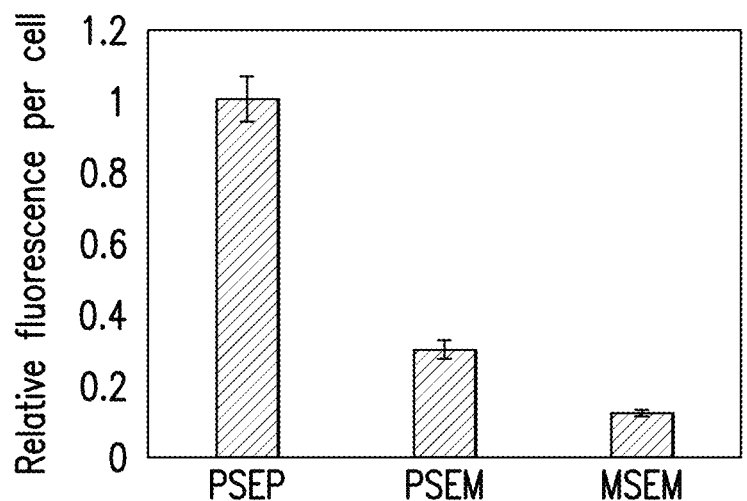

The binding and internalization between monovalent versus bivalent chimeras was compared using confocal fluorescence microscopy. An RNA aptamer specific to small organic dye Malachite Green (MG) (Grate, et al., *Proc Natl Acad Sci USA*, 96: 6131-6136 (1999)) with similar size and composition as A10-3.2 aptamer was selected as a non-targeting control. The chimera MSEM (MG aptamer-survivin siRNA-EGFR siRNA-MG aptamer) was constructed with the same length as PSEP. At the same time, the chimera PSEM (PSMA aptamer-survivin siRNA-EGFR siRNA-MG aptamer) which contains a functional PSMA aptamer and a negative control aptamer was established as a monovalent chimera control bearing the same size as PSEP. The one strand (aptamer-survivin antisense) of chimeras were labeled with Cy3-CTP during transcription and used to treat C4-2 cells, a PSMA-positive PCa cell line, for 2 h at 37° C. At the same time, LysoTracker™ (spectrally distinguishable green fluorescence) was added into culture medium for exhibiting endosomes and lysosomes. As shown in FIG. 1E, the density of bivalent PSEP internalized into the cytoplasm within 2 h is significantly higher than that of monovalent PSEM, and non-targeting MSEM. PSEM mainly resides on the membrane surface, in contrast, bivalent-PSMA aptamer chimera is able to broadly distribute inside cytoplasm with some around the nucleus. The fluorescence intensity of each chimera was evaluated by ImageJ™. The results (FIG. 1F) showed that PSEP treated-cell contained about 2-fold increased fluorescence than PSEM, and about 7-fold increased fluorescence than non-targeting MSEM.

Figure 1G:
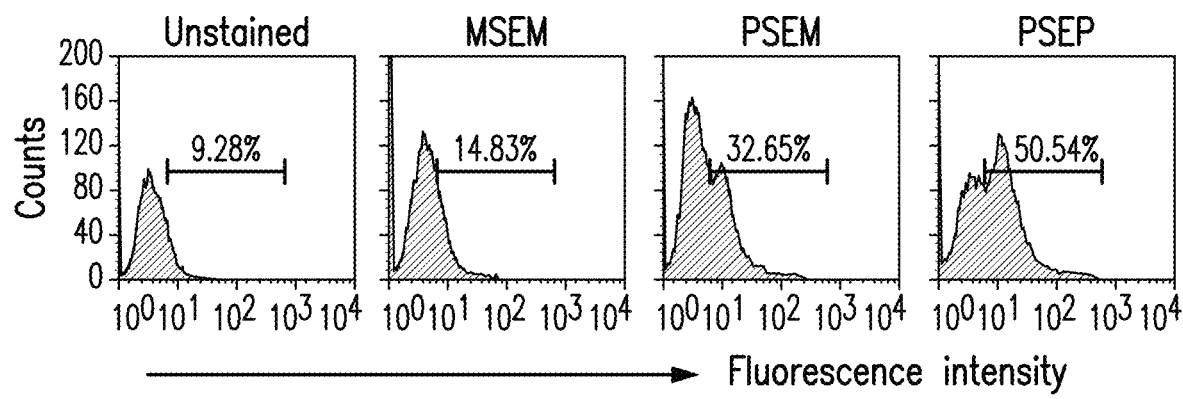

Furthermore, quantitative flow cytometry was performed to compare the internalization. C4-2 cells were treated with Cy3-labeled chimeras followed by 0.5 M NaCl-DPBS washing to remove surface bound chimeras. The amount of internalized chimeras was quantitated using flow cytometry. As shown in FIG. 1G, the fluorescence intensity in PSEP treated C4-2 cells have increased about 1-fold compared with that in PSEM-treated cells, after subtracting nonspecific MSEM binding. Taken together, these results confirm the advantage of bivalent aptamer over the monovalent counterpart in siRNA internalization.

Example 4: PSEP Chimera-Mediated Cell Type-Specific Knockdown of Target Genes

Materials and Methods

Western blot. Cells were lysed in lysis buffer (M-PER Mammalian Protein Extraction Reagent, Thermo Fisher Scientific) containing 1×Halt Protease Inhibitor Cocktails. The cell lysates were kept on ice for 40 min and vortexed for 3 times and centrifuged at 12,000×g for 10 min at 4° C. The supernatant was collected and the protein concentration was determined with Bio-Rad Protein Assay (Bio-Rad, Hercules, Calif.). Protein (100 µg) was mixed with 2× Laemmli sample buffer containing 5% β-mercaptoethanol and heated at 95° C. for 10 min. Denatured samples was separated on 10% SDS-polyacrylamide gel and transferred to PVDF membrane. The membranes were blocked with 5% non-fat milk overnight at 4° C., and then incubated with primary antibodies for 2 h at room temperature, followed by incubation with horseradish peroxidase-conjugated secondary antibodies for 2 h at room temperature. After ECL Western Blotting Substrate (Pierce) was added onto membrane, the signals were captured by the exposure to X-ray film. Western blot was quantified using ImageJ (NIH).

Cell Type Specific Binding Assay.

C4-2, PC3, BXPC3 and T24 cells were trypsinized and washed with PBS. After washing, cells were incubated with Cy3-labeled PSEP (50 nM) or Cy3-labeled MSEM (50 nM) in the presence of yeast tRNA (300 µg/ml) for 30 min at 37° C. Cell binding were detected using BD FACSCalibur flow cytometry.

Results

Figure 2A:
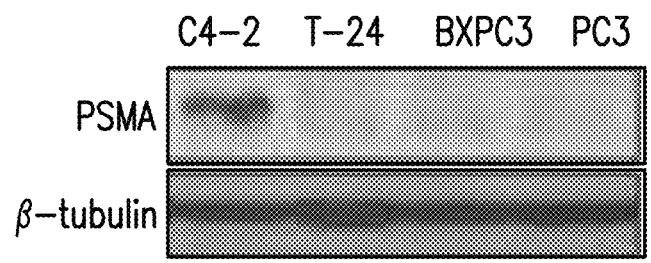
FIGS. 2A-2J refer to the characterization of PSEP on cell-specific binding, gene knockdown, and cytotoxicity.
Figure 2B:
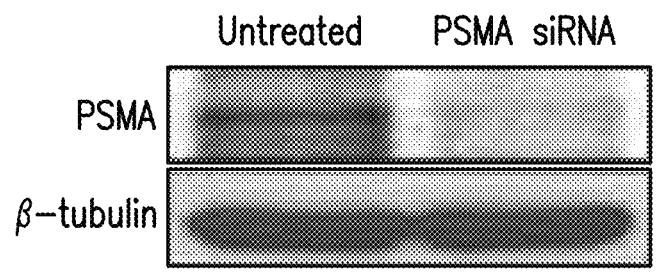
Figure 2B:
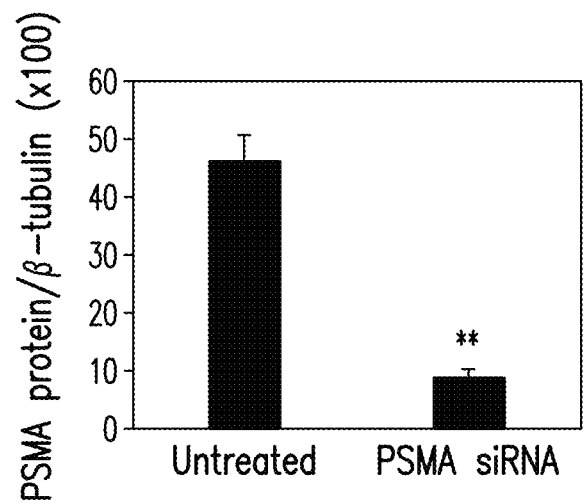
Figure 2C:
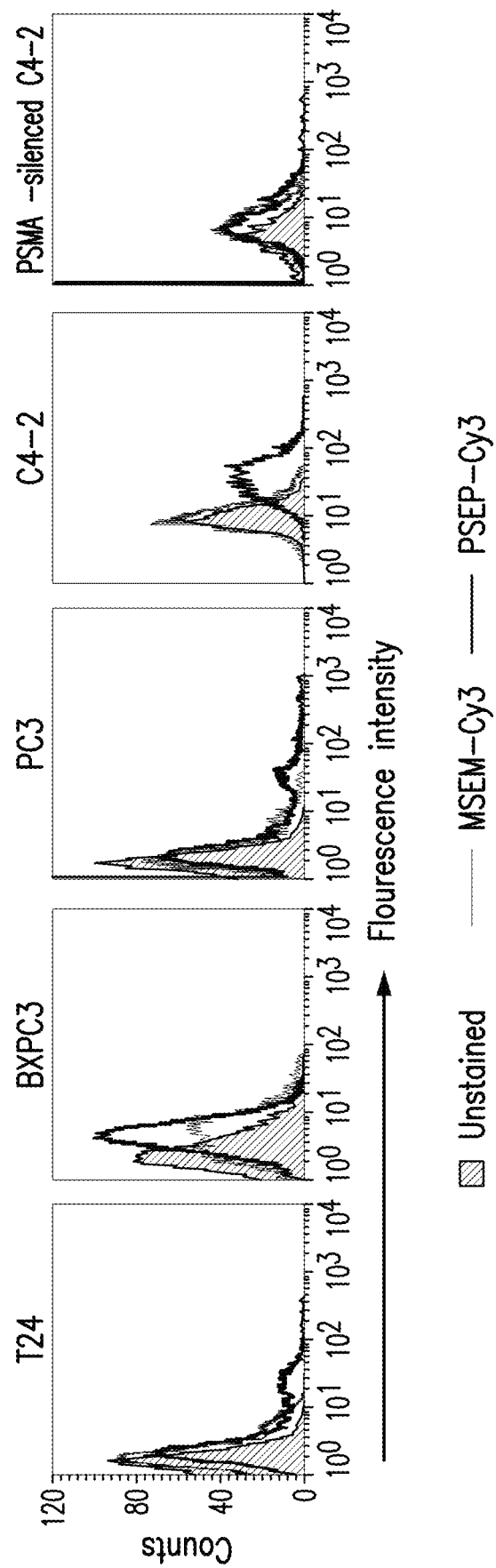

Four cell lines were examined on the expression of PSMA with Western blot. Three cancer cell lines including PC3 (prostate), BXPC3 (pancreatic) and T-24 (bladder) are negative for PSMA, while C4-2 cells have strong PSMA expression (FIG. 2A). Furthermore, the binding specificity of PSEP chimera on different cell lines was evaluated. The flow cytometry demonstrated that PSEP chimera has specific binding capability on PSMA-expressing C4-2 cells, but not PSMA-negative BXPC3, PC3 and T-24 cell lines (FIG. 2C). To further validate whether PSMA aptamer indeed binds to PSMA protein, PSMA was knocked down with PSMA siRNA, as shown in FIG. 2B. After 72 h transfection of PSMA siRNAs by lipofectamine RNAi MAX, Western blot was performed and proved the PSMA knockdown.

Next, flow cytometry was performed to evaluate the aptamer binding. The result indicates that PSEP significantly reduces the staining for C4-2 cells (FIG. 2C), which confirms A10-3.2 aptamer possesses PSMA-specific binding capability.

Figure 2D:
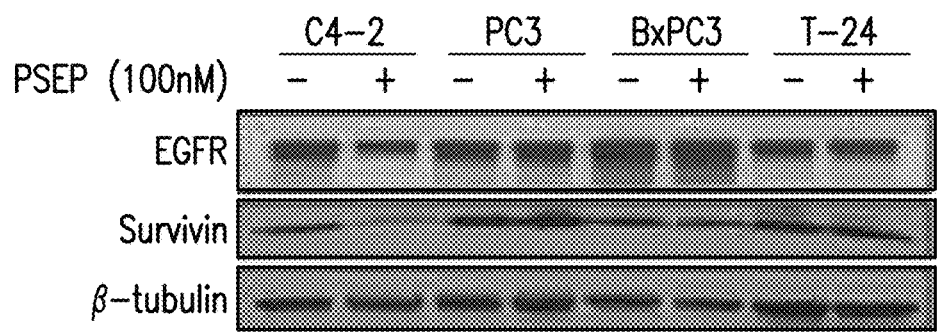
Figure 2E:
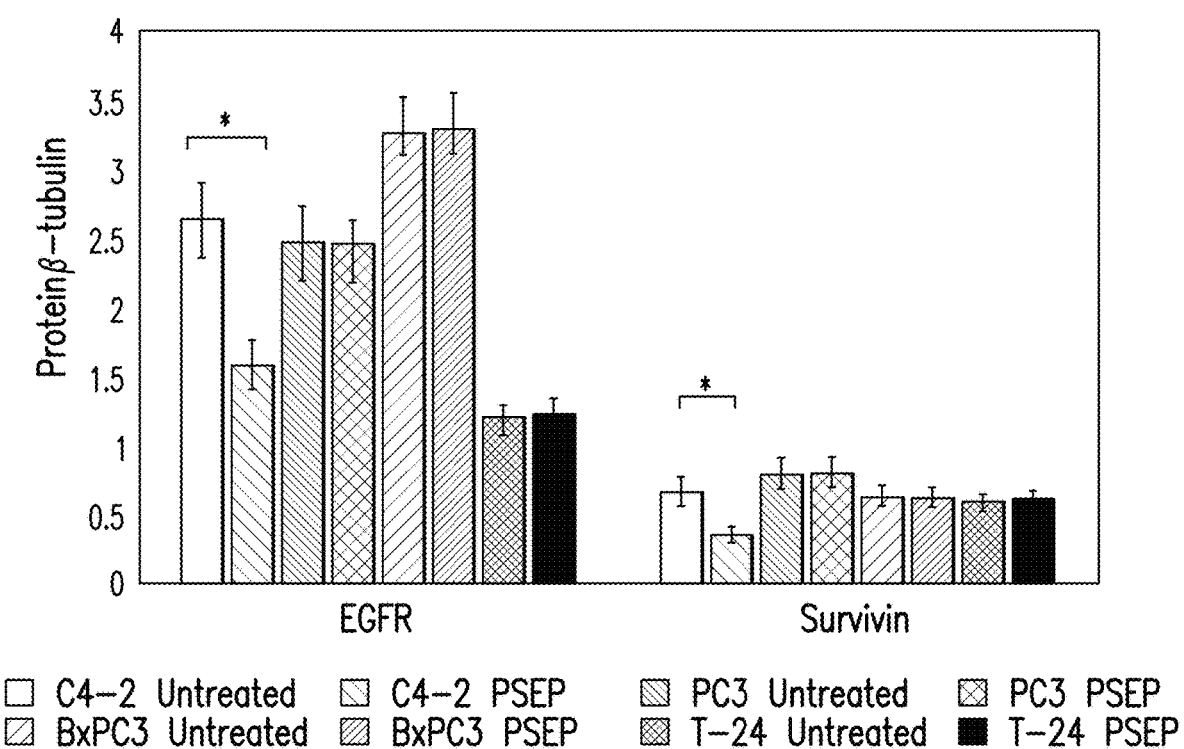
Figure 2F:
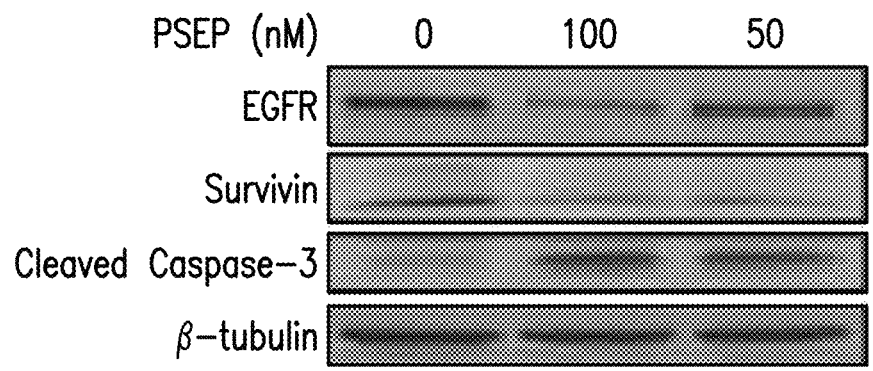
Figure 2G:
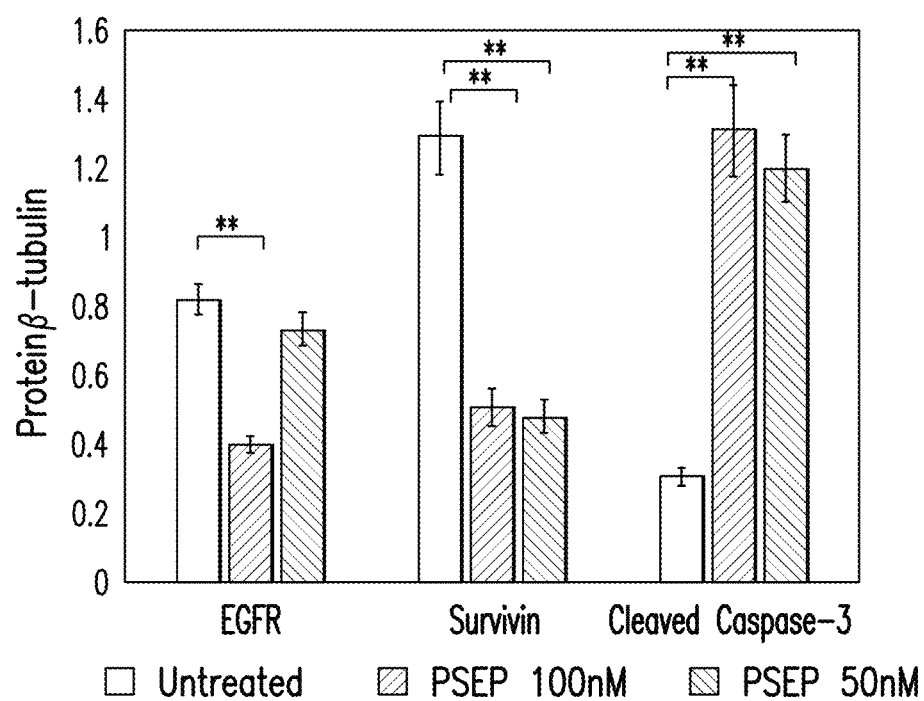

Next, cell lines were treated with PSEP for 72 h, and expression levels of EGFR and survivin were determined by Western blot. As shown in FIGS. 2D and 2E, in PSMA-expressing C4-2 cells, the protein levels of EGFR and surviving have been significantly reduced compared with the untreated C4-2 cells. In contrast, there are no detectable suppression of EGFR and survivin in PSMA-negative cells lines including PC3, BXPC3 and T-24. The results indicate that PSEP, but not MSEM, MG aptamer or scrambled siRNA control, is able to co-deliver two siRNAs and concomitantly silence two target genes in a cell type-specific manner. Furthermore, PSEP treatment resulted in a dose-dependent increase in cleaved capase-3, an indicator of apoptosis (Porter, et al., *Cell Death Differ,* 6: 99-104 (1999)) (FIGS. 2F and 2G). The results suggest that the silencing of EGFR and survivin by PSEP is associated with activated apoptotic signaling in PSMA-positive cancer cells.

Next, the silencing efficacy of siRNAs was evaluated in each construct by lipofectamine transfection. Conventional lipofectamine-based transfection is independent of aptamers and allows comparison to the native silencing efficacy of siRNAs. Gene silencing of EGFR and survivin in PSMA positive C4-2 and PSMA-negative PC3 cells were evaluated with Western blot. In C4-2 cells, the siRNAs in each chimera have well preserved their native silencing efficacy compared with EGFR siRNA and survivin siRNA.

Transfected PSEP can silence 80-90% of EGFR and 85-95% of survivin, while PSEP without lipofectamine can silence 40-50% of EGFR and 50-60% of survivin. Chimeras of PSEM, PSEM and MSEM showed the very similar efficacy in silencing EGFR (80-90%) and survivin (85-95%) by lipofectamine transfection. In PC3 cells, PSEP without lipofectamine did not silence EGFR or survivin, suggesting cell specificity of PSEP. By lipofectamine transfection, all constructs have achieved gene knockdown at similar levels to the native EGFR siRNA and surviving siRNA. In lipofectamine transfection experiments, all constructs are free labeled and present with native structures. PSEP with or without 2'-fluororine modification showed the very similar silencing efficacy by lipofectamine transfection.

Example 5: PSEP Chimera-Mediated Cell Type-Specific Cytotoxicity

Materials and Methods

Cytotoxicity assay. Cellular cytotoxicity was quantified by measuring WST-8 formazan using Cell Counting Kit-8 (CCK-8) (Dojindo, Japan). Cells in RPMI 1640 containing 5% fetal bovine serum were seeded in 96-well plate at a density of $5 \times 10^3$ in 5% $CO_2$ incubator for 24 h at 37° C. Cell lines of C4-2, PC3, BXPC3 and T24 were incubated with the varying concentrations of PSEP for 72 h without transfection reagents (e.g., Lipofectamine™).

Results

Figure 2H:
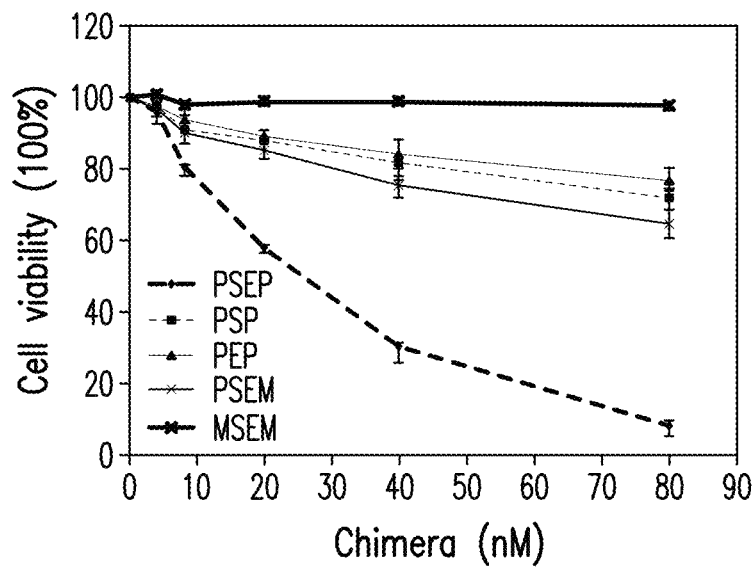
Figure 2I:
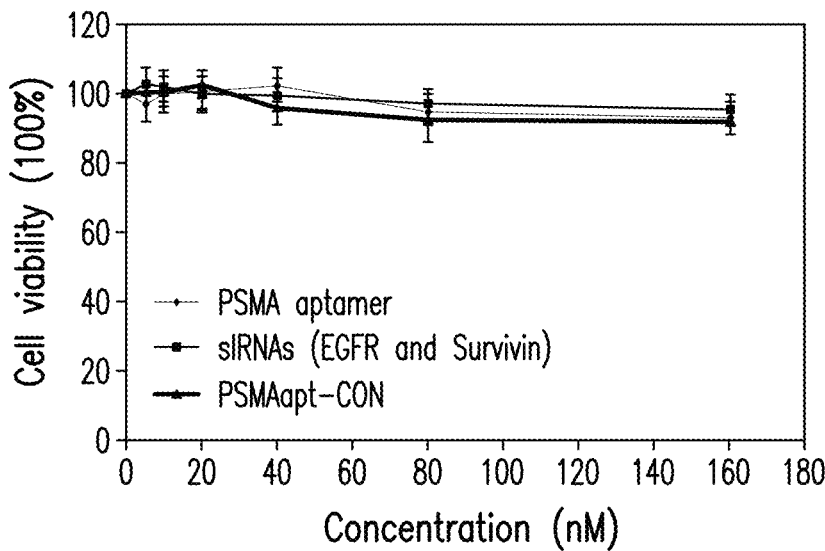

To assess cell viability in the presence of PSEP, PSEM, MSEM, PEP and PSP, C4-2 cell lines were exposed to chimeras for 72 h at the varying concentrations (FIG. 2H). At the concentration of 80 nM, the reductions in C4-2 cell viability induced by individual aptamers are: about 92% (PSEP), 35% (monovalent PSEM), 25% (PSP), 21% (PEP), and 1% (MSEM), respectively. $IC_{50}$ of PSEP is about 26 nM. PSEP also showed the killing activity for PSMA positive LNCaP cells. In a set of control experiment (FIG. 2I), C4-2 cells were treated with PSMA aptamer, or mixed siRNAs specific to EGFR and survivin, or PSMAapt-CON chimera without targeting any mRNA, respectively. C4-2 cells did not have reduced cell viability when exposed to chimera alone, simply mixed siRNAs, or control chimera. The results suggest that PSMA aptamer alone does not have tumor killing activity, in agreement with previous studies (Dassie, et al., *Nat Biotechnol,* 27: 839-849 (2009); McNamara, et al., *Nat Biotechnol,* 24: 1005-1015 (2006)).

Figure 2J:
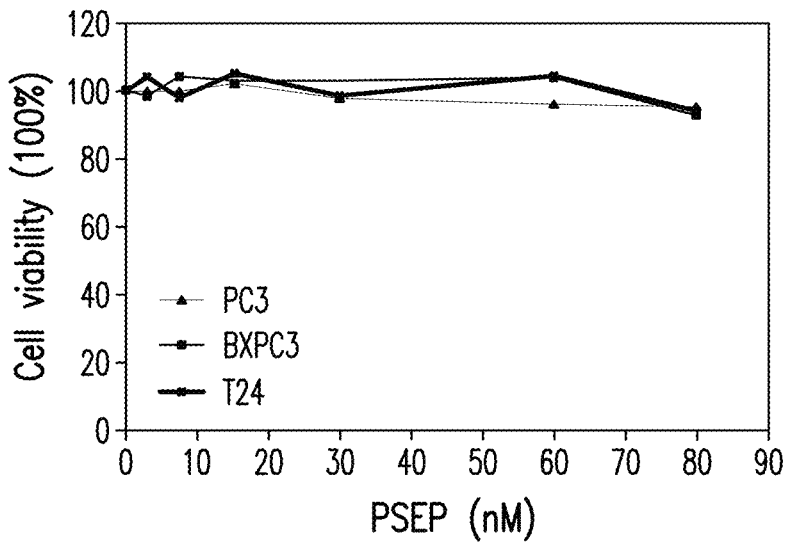

Since siRNA cannot diffuse freely through cell membrane, it is well known the delivery systems are needed to aid siRNA function. Therefore, it is not surprising that simply mixed siRNAs without a carrier are ineffective for cell killing. Furthermore, three PSMA-negative cancer cell lines (PC3, BXPC3 and T-24) were treated with varying concentrations of PSEP. The result shows that three PSMA-negative cancer cell lines do not respond to the PSEP treatment and there was no significant changes in cell viability upon PSEP treatment (FIG. 2J). The viability assay suggests potentially lower side effects in vivo.

Furthermore, cytotoxicity was evaluated after lipofectamine transfection of each constructs. The $IC_{50}$ is about 11-13 nM for PSEP, MSEM and PSEM, 20 nM for PSP, and 40 nM for PEP, respectively. As the controls, PSMA and PSMA-CON did not show any cytotoxicity, and the $IC_{50}$ is 18 nM for survivin siRNA, 38 nM for EGFR siRNA, and 28 nM for equal molar mixed survivin and EGFR siRNAs. For comparing cytotoxicity of PSEP in different cell lines, PC3, BXPC3 and T24 were treated with varying concentrations of PSEP. The $IC_{50}$ is about 24 nM in PC3 cells, 41 nM in BXPC3 cells, while 74 nM in T24 cells, respectively. These experiments confirm that siRNAs inserted into chimeras have well preserved silencing effect and potent cytotoxicity. PSEP without lipofectamine has less efficacy than transfected PSEP. The significantly different $IC_{50}$ for transfected PSEP in different cell lines indicates the each tumor has different survival pathways.

Example 6: PSEP-Induced Time-Dependent Apoptosis in C4-2 Cells

Materials and Methods

Detection of apoptosis by flow cytometry and fluorescent microscopy. C4-2 prostate cancer cells were seeded onto cover glass for florescence imaging and into 12-well plates for flow cytometry. C4-2 cells ($2 \times 10^6$) were treated with PSEP (100 nM) for different time durations. The cells were harvested and washed in cold phosphate-buffered saline (PBS). Cells were stained with Alexa Fluor 488 Annexin V-Propidium Iodide (PI) solution for 15 min at room temperature. For imaging, fluorescence microscopy (Nikon Eclipse TE2000-S) was used to capture each channel signals separately and merged with ImageJ Plugin for colocalization. For flow cytometry, cells ($1 \times 10^4$/sample) were acquired by BD FACSCalibur and analyzed using BD FACStation software.

Results

Figure 3A:
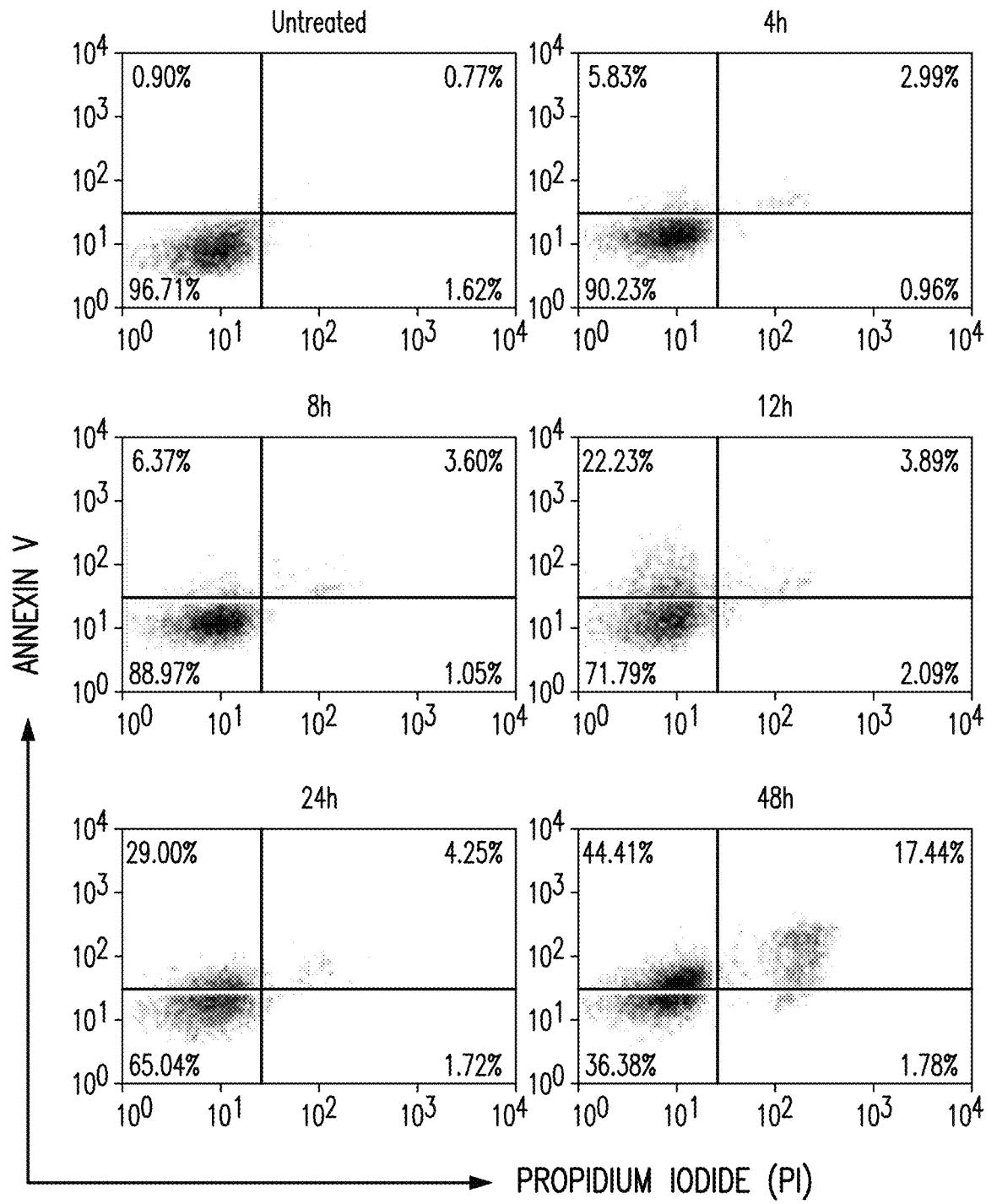
FIGS. 3A and 3B show the detection of apoptosis with flow cytometry and fluorescence microscopy. C4-2 cells were treated with PSEP for the varying durations.
Figure 3B:
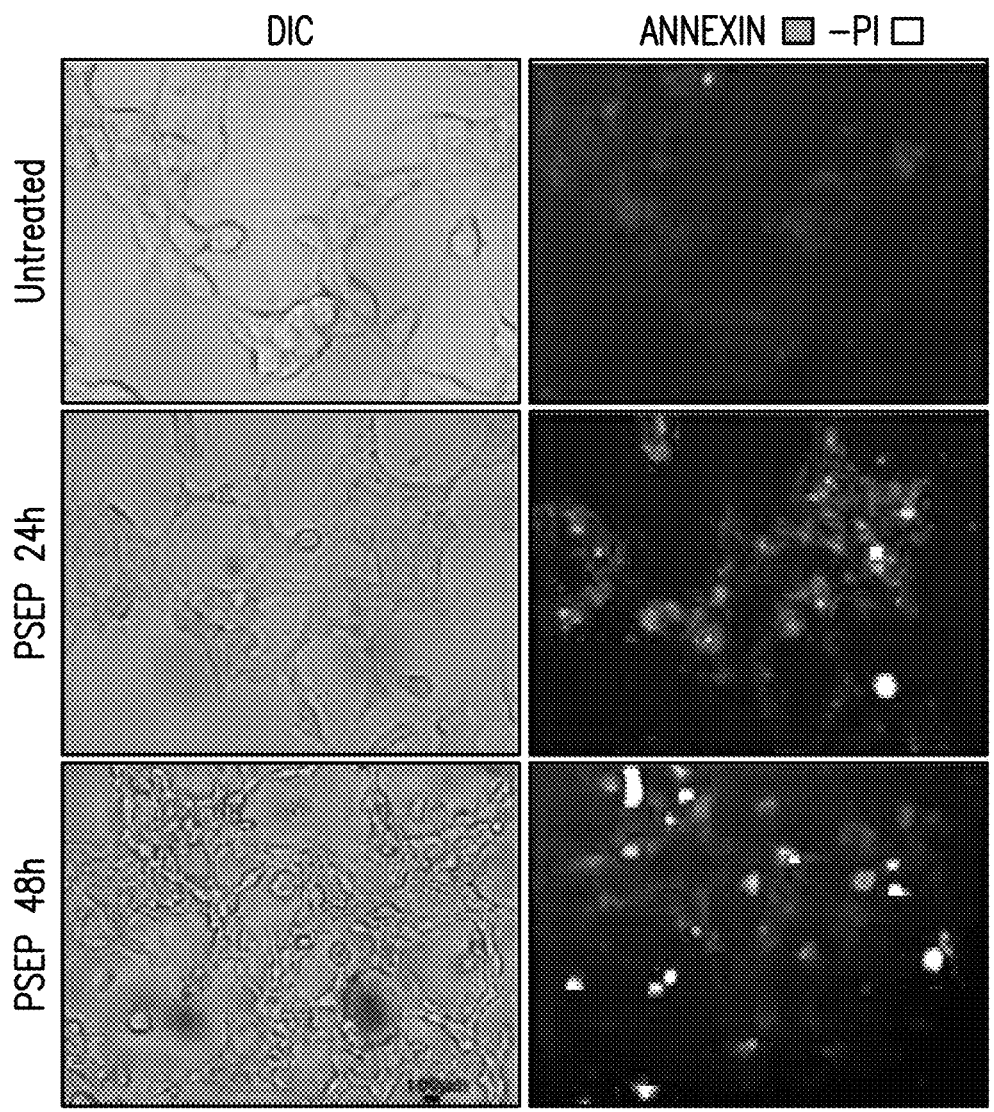

To further confirm apoptosis occurrence upon PSEP treatment, flow cytometer was performed to monitor the dynamic process of cell death. First, C4-2 cells were exposed to PSEP for different time durations (4-48 h). Apoptosis events were detected using Annexin V-Propidium Iodide (PI) staining. In a time-course measurement, as shown in FIG. 3A, after 4-h treatment, there was an increase in early apoptotic cell population (Annex V+PI−) from 0.90% without treatment to 5.83% with treatment, and an increase in the late apoptosis (Annex V+PI+) from 0.77% to 2.99%. After 12 h, entire population apparently moved toward to early apoptosis, quantitatively, 22.3% of cells are at the stage of early apoptosis, 3.89% at the stage of late apoptosis. After 24 h, 29% cells are at the early apoptosis and 4.25% at the late apoptosis. Up to 48 h, the early apoptotic cells increased to 44.41% and late apoptotic and dead cells increased to 17.44%. C4-2 cell population in the presence to PSEP progressed from viable, early apoptosis to the late apoptosis. This "stage movement" of C4-2 cells after PSEP treatment indicates that PSEP suppresses C4-2 cell survival through apoptosis, which is directly related to downregulation of EGFR and survivin. There were consistent changes in cell morphology and apoptotic pattern, as identified from fluorescence microscope imaging (FIG. 3B). Compared with untreated control, most cells have increased Annexin V signal (green) after 24 h treatment, and at 48 h, increased PI signal (red) were observed. Cell morphology showed shrinkage and optically dimmer compared with untreated control cells.

Example 7: Reduction of Tumor Burden and Inhibition of Tumor-Associated Neovasculature by Systemic Administration of PSEP Materials and Methods Xenograft models. 4 to 5-week-old male athymic nu/nu mice were injected subcutaneously with C4-2 cells ($2 \times 10^6$) mixed with matrigel (v/v 1:1) (Corning, N.Y.) at the left flank of mice. Upon tumor reaching 100 mm3, mice were randomly divided into three groups. PSEP (100 µl, 20 µM) or PSMA-CON (100 µl, 40 µM), or MSEM (100 µl, 40 µM) or PBS (100 µl) was intraperitoneally injected into the mice every other day for 7 days and followed by injection every day for 14 days. Tumor sizes and body weights were measured twice a week. The tumor volume was calculated according to the formula: $V=(L \times W2)/2$ (W, the width; L, length). The animals were euthanized two days after the last treatment. The tumors and organs (liver, spleen, kidney, brain, heart, muscle, blood and intestine) were removed and fixed in 10% formalin buffer. The sections of tissues were analyzed by hematoxylin and eosin (H&E) staining and immunohistochemistry.

Histology Assay.

Animals were euthanized with $CO_2$, and tumors and organs (spleen, lung, kidney, intestine, heart, liver and brain) were removed and fixed with 4% paraformaldehyde in 0.1 M sodium phosphate buffer (PH 7.6). Tissues were cut into 3 mm sections and were dehydrated in graded series of alcohol and xylene, and embedded in paraffin. Sections (6 µm) were cut and mounted on the slides, deparaffinized in xylene and ethyl alcohol. Each block has a section for H&E staining. For immunohistochemistry assay, sections were incubated in 3% normal goat serum for 2 h and followed by overnight incubation with primary antibodies:caspase-3 (1:20), survivin (1:800), EGFR (1:50), HIF1α (1:100), Ki67 (1:100), P21(1:100) and CD31 (1:25). After washing, the sections were incubated with biotinylated secondary antibody (1:200, VECTOR, Burlingame, Calif.) for 1 hour. Following washing, the sections were incubated with VECTASTAIN ABC reagents for 30 min. The immunoreactivity (IR) was visualized with the substrate solution (VECTOR). The images were captured with Nuance fluorescence microscope with bright field imaging system. TUNEL assay was performed according to the manufacturer's instruction. Paraffin embedded tissues were sectioned, dewaxed, hydrated and digested with Proteinase K. After washing, slides were immersed into quenching solution for 5 min, then incubated with TdT labeling buffer for 1 h in a humidity chamber. Slides were washed in PBS and incubated with streptavidin-HRP for 10 min. After washing, DAB work solution was added into the slides. Following washing, slides were counterstained with Methyl Green. The images were captured with Nuance fluorescence microscope.

Results

Figure 4A:
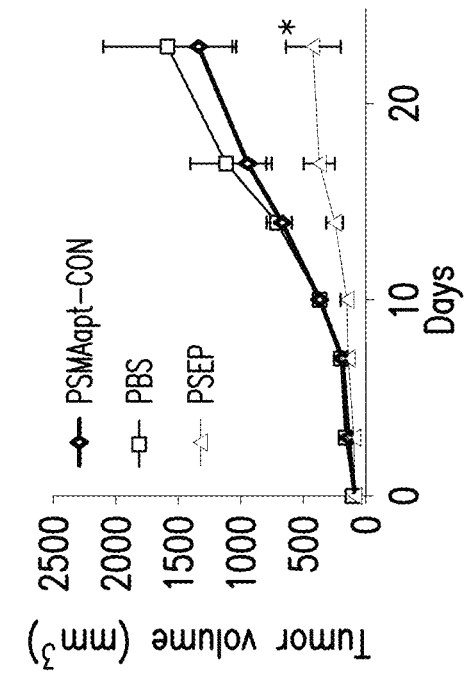
FIGS. 4A to 4C refer show that systemic administration of PSEP significantly suppresses tumor growth and reduces tumor-associated angiogenesis.
Figure 4C:
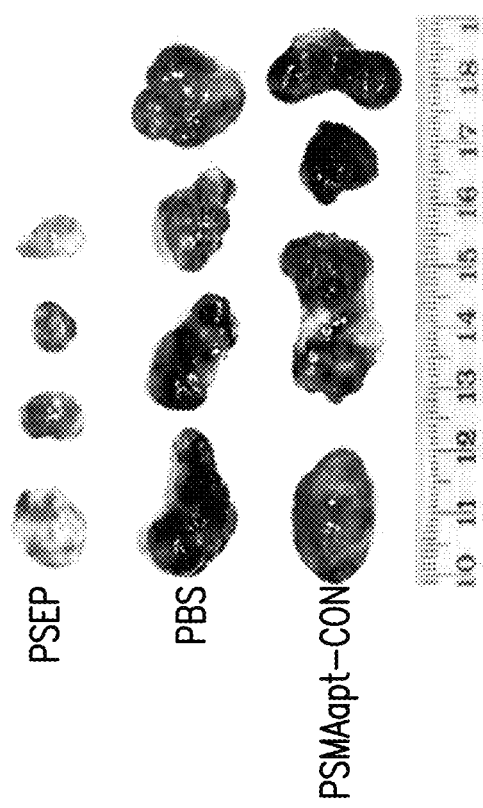
Figure 4B:
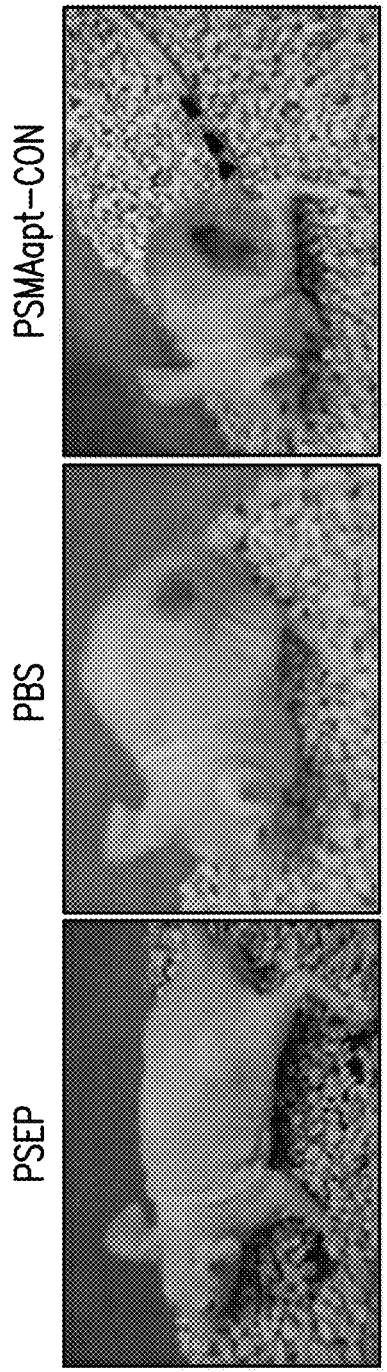

To assess the impact of PSEP on PCa growth in vivo, subcutaneous C4-2 xenografts were established in athymic nu/nu male mice. PSEP (100 µl, 20 µM) per mouse were injected intraperitoneally to tumor-bearing mice every other day for beginning 1 week and every day for the following two weeks. Control mice were injected intraperitoneally with equivalent volume of PBS or PSMAapt-CON (100 µl, 40 µM) (i.e., at the same moles of aptamer and siRNA as PSEP). Following a 21-day treatment, 3-4 fold reduction in tumor volume was observed upon treatment with PSEP, as compared with the tumors treated with PBS or non-silencing PSMAapt-CON (FIGS. 4A and 4C). Notably, the color of C4-2 xenograft was significantly changed after treatment. In live mice, a clear blue color in the PBS- and PSMAapt-CON-treated mice has changed to a pale-to-white color in PSEP-treated mice (FIG. 4B). Consistently, from macroscopic observation, freshly dissected ex-vivo tumors showed visible difference in color and size after PSEP treatment versus those in the tumors treated with PBS and PSMAapt-CON. Tumors from PBS- and PSMAapt-CON-treated mice were dark, bloody and highly vascularized, in contrast, tumors from PSEP treated mice were pale and poorly vascularized. These results suggest that PSEP may have inhibitory effect on angiogenesis of C4-2 tumors. In another cohort animal experiment, mice were treated with MSEM (100 µl, 20 µM) or PBS (100 µl) every other day for 7 days followed by injection every day for 14 days. Using tumor size as the indicator, no significant efficacy was observed upon the treatment with MSEM chimera.

Example 8: Assessment of Anti-Angiogenesis Effect of PSEP

Materials and Methods

VEGF Assay.

C4-2 cells were seeded into 24-well plates at the density of 1×106/well for 24 hours in the 5% $CO_2$ incubator at 37° C. The culture medium was changed to serum free. The PSEP with the varying concentrations were added into the culture. After 72-h incubation, the cell culture supernatants were collected. The VEGF-A in supernatants was determined by human VEGF-A ELISA kit following the manufacture's instruction.

Results

Figure 5A:
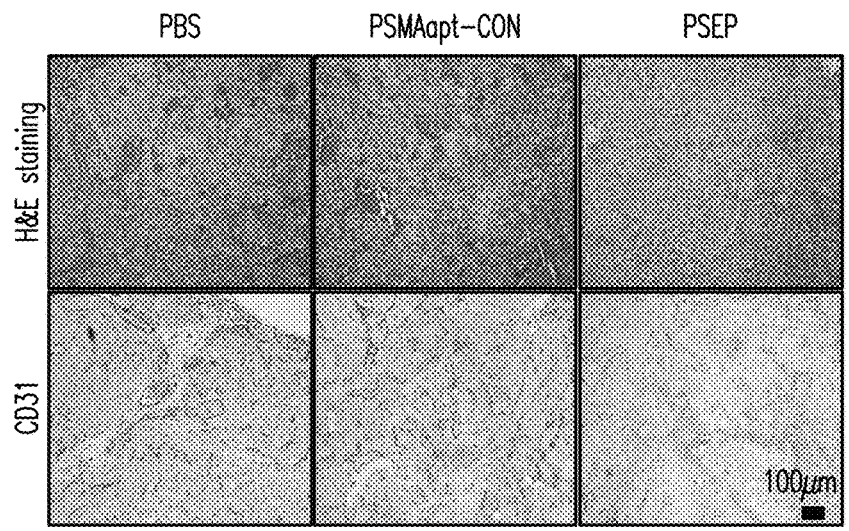
FIGS. 5A-5D show the histology analysis of tumors and identification of anti-angiogenesis effect of PSEP.

To confirm the anti-angiogenesis effect of PSEP, histology analysis was performed. Remarkably, H&E staining revealed that the blood vessel density has been significantly reduced after PSEP treatment compared with controls treated with PBS or PSMAapt-CON. The high-density blood vessels span the entire tumors in control mice, consistent with the observed blue color of these control tumors, whereas PSEP-treated tumors show much less blood vessels, consistent with the observed much lighter color of PSEP-treated tumors. CD31 immunohistochemistry (IHC) was performed to further demonstrate the change of microvessels after PSEP treatment. C4-2 tumors from PBS and PSMAapt-CON groups have densely distributed blood vessels; remarkably, a significant reduction in CD31-stained blood vessels was observed after administration of PSEP (FIG. 5A). The results suggest that PSEP is able to inhibit angiogenesis.

Figure 5B:
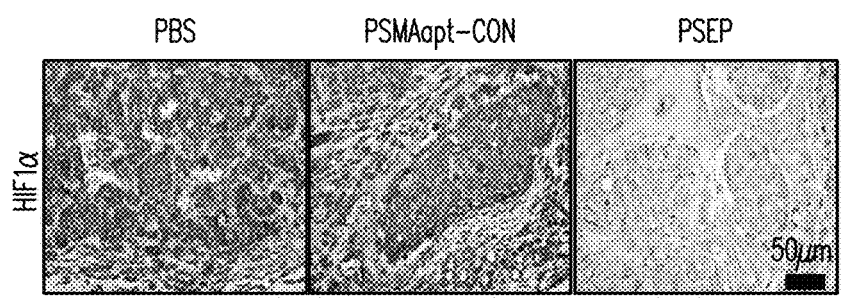
Figure 5C:
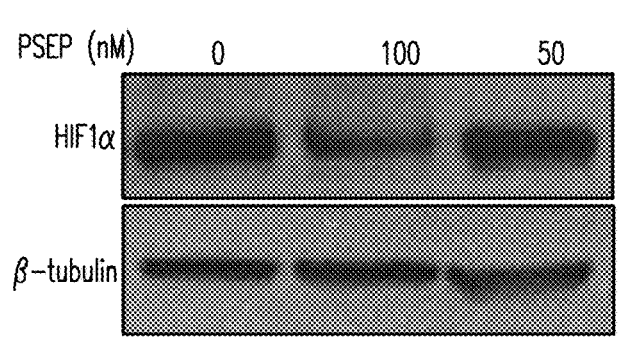
Figure 5D:
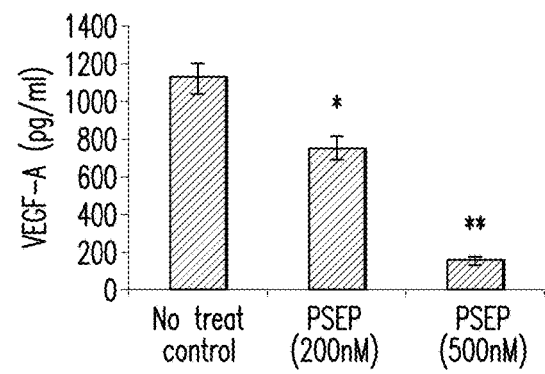
Figure 6:
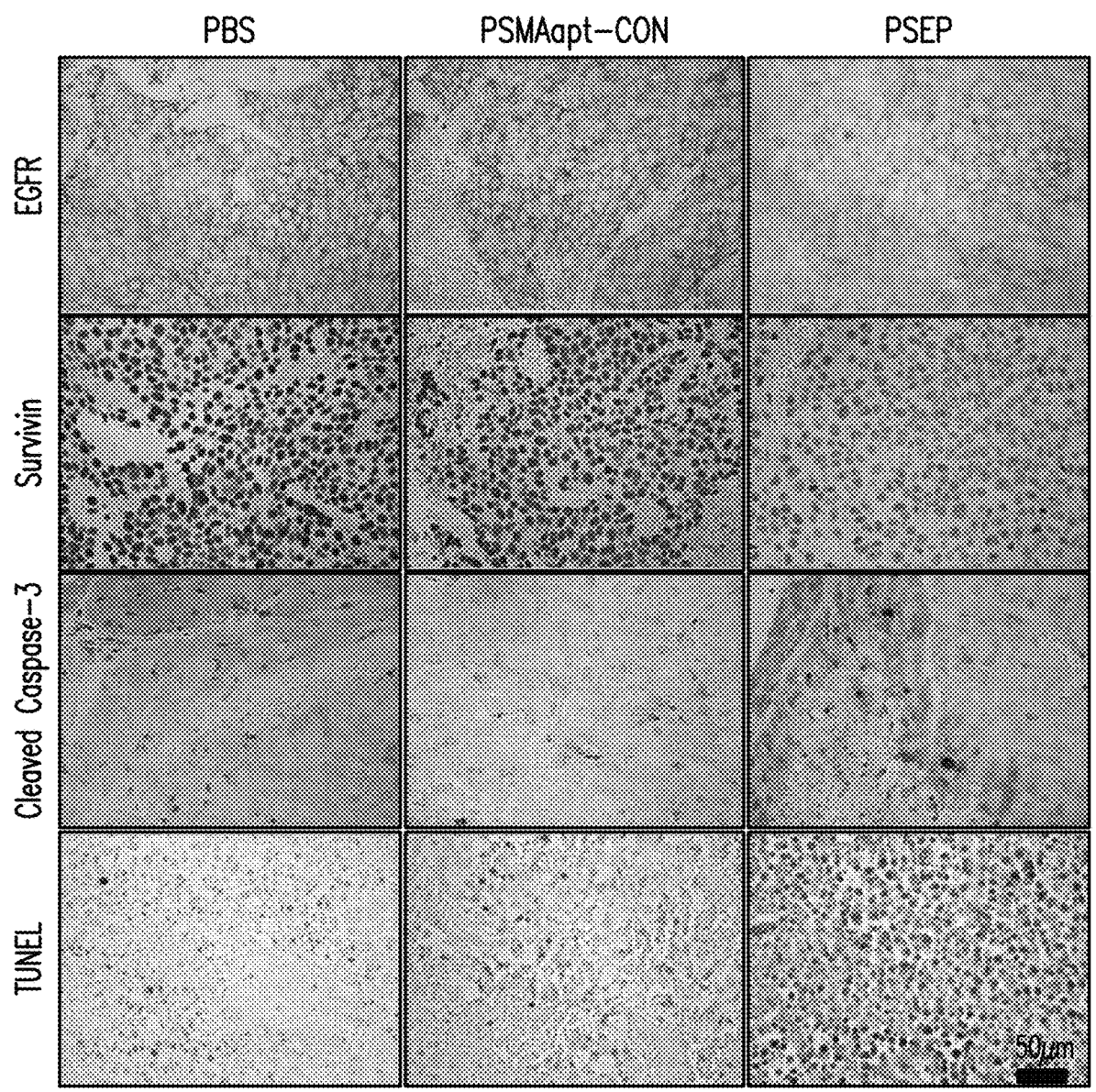
FIG. 6 is a panel of images showing the evaluation of gene expression and apoptosis after PSEP treatment in vivo. Formalin-fixed paraffin-embedded sections of xenograft tumors were stained with antibodies targeting EGFR, survivin, cleaved caspase-3. TUNEL assay was performed to detect the apoptosis-associated DNA damage. Comparing with PBS and PSMAapt-CON, PSEP treatment has significantly reduced the expression of EGFR and survivin, and significantly up-regulated cleaved Caspase-3. TUNEL assay further revealed the much stronger DNA damage in PSEP treatment tumors than that in controls. Scale bar, 50 μm.

Tumor angiogenisis heavily depends on the growth factors released from tumor cells, since the growth factors will target on endothelial cells and stimulate the growth of host blood vessels. C4-2 cells are able to secret high level of VEGF-A52, which contributes to the development of vascularized tumors in animal models. To determine whether PSEP inhibits angiogenesis through a VEGF-dependent mechanism, C4-2 cells were treated with PSEP for 72 h, the cuture supernatants were colleceted and analyzed with VEGF-A ELISA kit. VEGF-A in untreated controls is 1100±70 pg/ml, and reduced to 755±55 pg/ml (decrease by 31%) upon 200 nM PSEP treatment, and was further reduced to 161±15 pg/ml (decrease by 85%) upon 500 nM PSEP treament (FIG. 5D). The mecahnism by which PSEP inhibits VEGF angiogenesis was investigated further. It has been reported that EGFR promotes the expression of VEGF and activates autocrine VEGF signaling in endothelia cells[53]. In squamous cell carcinoma, it has been shown that EGFR inhibitors (gefitinb and erlotinb) decrease VEGF expression via Hypoxia-inducible factor 1-alpha (HIF1α), a direct upstream regulator for VEGF transcription. To evaluate if EGFR silencing has an effect on HIF1α, IHC was employed to detect HIF1α in tumor tissues and ELISA was used to detect HIF1α in cultured C4-2 cells. Consistently, both methods confirmed the decrease of HIF1α after PSEP treatment (FIGS. 5B and 5C). Taken together, these results suggest that the anti-angiognesis effect of PSEP is, at least partially, mediated through an EGFR-HIF1α-VEGF pathway.

Example 9: Gene Silencing and Tumor Cell Apoptosis In Vivo

Gene regulation and apoptosis were evaluated in vivo. PSEP treatment significantly inhibited the expression of EGFR and survivin compared with PBS and non-silencing PSMAapt-CON, and consistently, dramatically upregulated cleaved formed Caspase-3. Furthermore, TUNEL (terminal deoxynucleotidyl transferase-mediated dUTP nick end-labeling) was performed to in situ detection of apoptosis-triggered DNA fragmentation in tumor tissue, which represents a characteristic hallmark of apoptosis. PSEP treated tumors have much stronger TUNEL staining than that of PBS- and PSMAapt-CON-treated tumors. IHC staining also demonstrated that PSEP can significantly increase P21 and reduce Ki67. The histology results indicate that PSEP enables the knockdown of EGFR and survivin and induces tumor cell apoptosis in vivo, which is translated into a significant suppression of tumor growth in xenograft prostate cancer.

Example 10: Immunogenicity and Toxicity

Figure 7A:
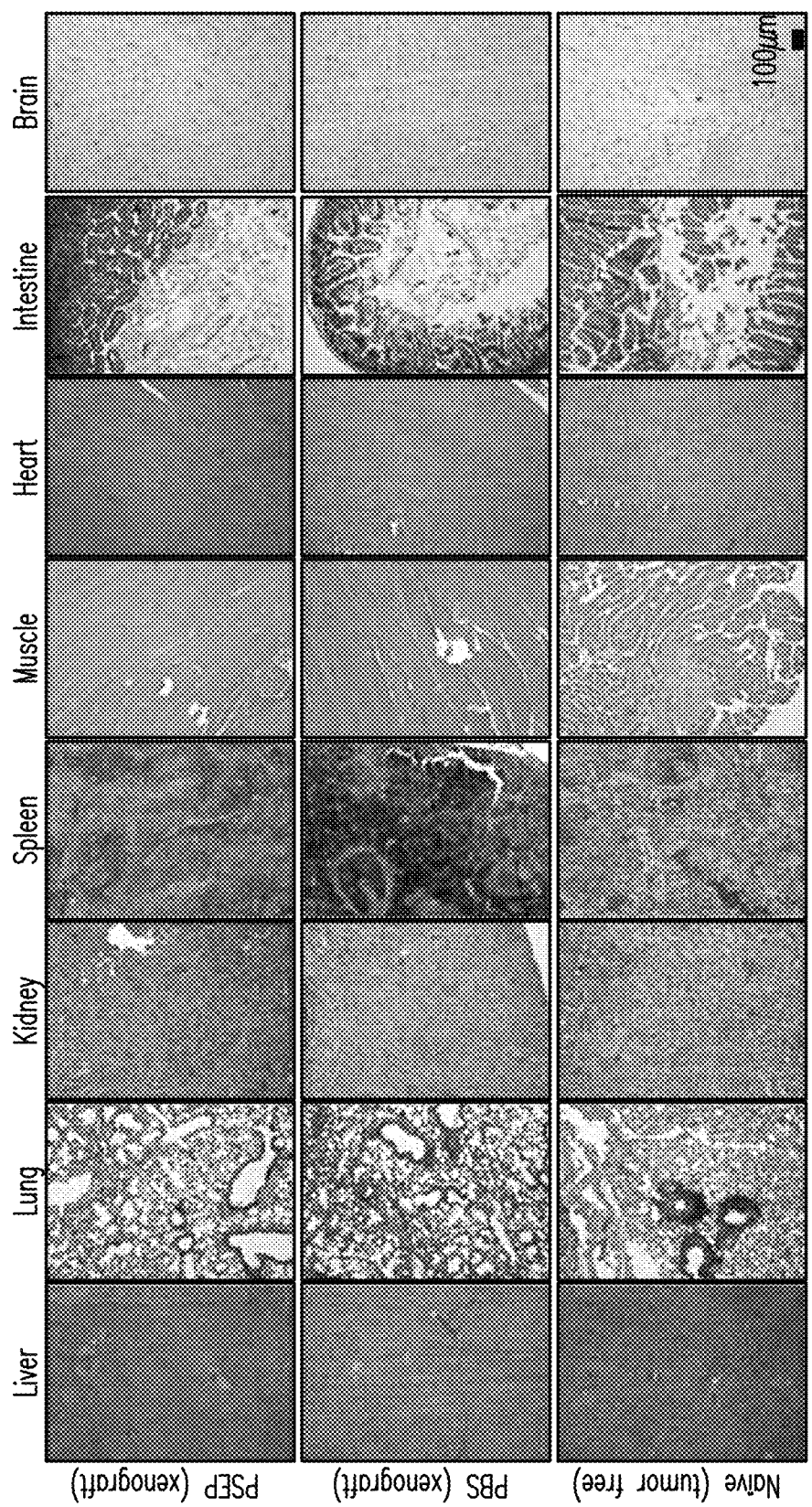
FIGS. 7A-7C refer to immunogenicity and toxicity experiments.
Figures 7B, 7C:
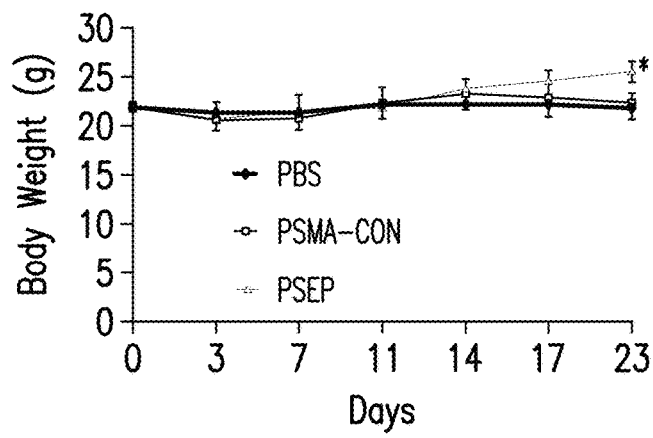
Figure 8A:
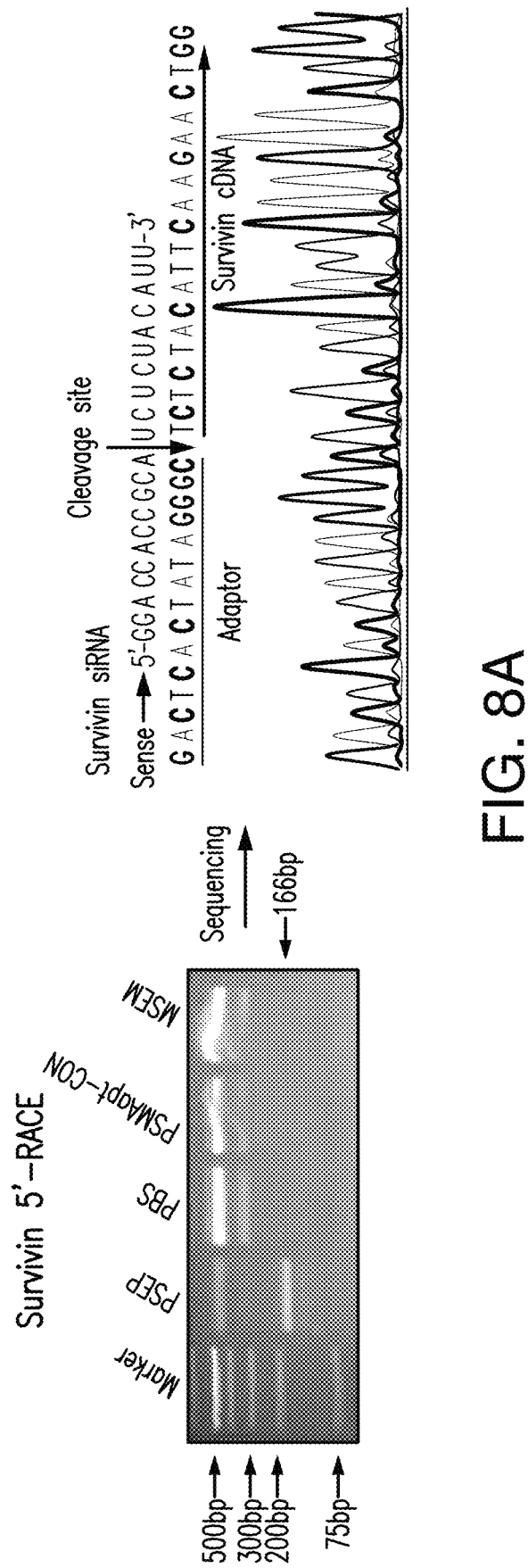
FIGS. 8A-8B refer to the 5'-RACE PCR assay to evaluate PSEP mediated gene silencing through RNAi pathway. Tumor RNA was extracted and transcribed into cDNA with a SMARTerIIA oligonucleotide adaptor. Nested PCR was performed to amplify gene products specific to EGFR and survivin. PCR products with expected sizes were sequenced. The cropped gel is used in the main figures.
Figure 8B:
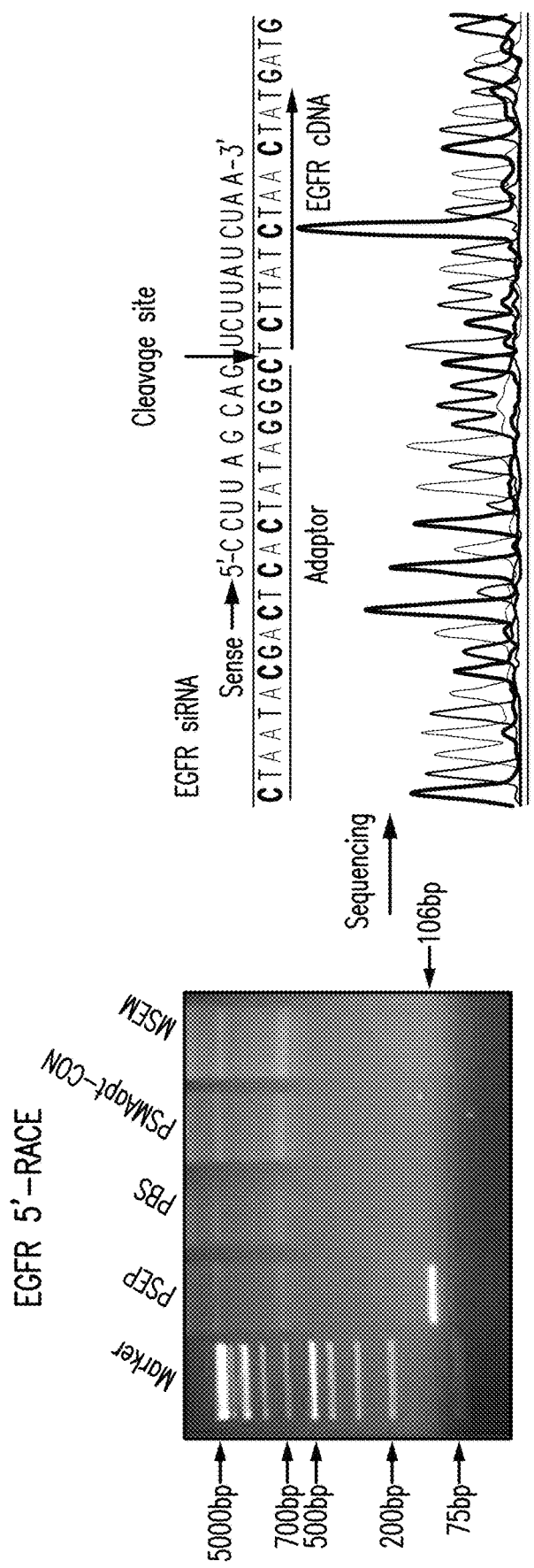

The histopathology of major tissues of xenografts were evaluated after administering PSEP, or equivalent volume of PBS as well as naïve tumor-free mice. H&E staining showed that there are no differences in major organs among PSEP-, PBS-treated or naïve mice. The body weights in the PSEP treated group were higher than controls (PBS and PSMAapt-CON) (FIG. 7B). The body weight gain reflects the global improvement after PSEP treatment, and it clearly has no acute toxicity. It was reported that siRNA or siRNA/carriers can stimulate sequence-dependent innate immune responses associated with interferon-α (IFN-α) (Judge, et al., Nat Biotechnol, 23: 457-462 (2005)). Therefore, IFN-α releasing was measured using human peripheral blood mononuclear cells (PBMCs) following PSEP challenge for 5 h and 24 h. As shown in FIG. 7C, no positive IFNα signals were detectable in PBMCs.

Serum IFN-α and IL-6 was measured between PBS- and PSEP-treated mice. All IFN-α levels from PBS- and PSEP-treated mouse sera were undetectable and within the background levels, and IL-6 between PBS and treated mice did not show a statistical difference. These results suggest that PSEP RNA chimera does not trigger innate immune response and also does not have acute toxicity.

Example 10: 5-RACE (Rapid Amplification of cDNA Ends) Detection of PSEP Directed Gene Silencing Through RNAi Pathway Materials and Methods 5'-Rapid Amplification of cDNA Ends (5'-RACE) PCR Analysis.

5'-RACE was performed using SMARTer RACES'/3' kit according to the manufacturer's protocol. RNA (3 µg each) from tumors treated with different chimeras was reverse transcribed into cDNA containing a SMARTerIIA oligo-nucleotide adaptor. Nested PCR was performed to detect the cleavage sites. For EGFR siRNA analysis, outer PCR was first run with EGFR reverse primer (5'-GGGCAGGTGTC-CTTGCACGT-3') (SEQ ID NO:35) and forward Universal Primer A Mix (UPM) (5'-CTAATA CGACTCAC-TATAGGGCAAGCAGT GGTATCAACGCAGAGT-3') (SEQ ID NO:36); then inner PCR was performed with EGFR reverse primer (5'-GCACGGCGCCATGCAGGATT TCCTGT-3') (SEQ ID NO:37) and forward primer Universal Primer Short (5'-CTAATACGACTCACTATAGGGC-3') (SEQ ID NO:38). For survivin analysis, outer PCR was first performed with survivin reverse primer (5'-TGCTAAGGGGCCCACAGGAAGGCTGGT-3') (SEQ ID NO:39) and forward primer: UPM; then inner PCR was performed with survivin reverse primer (5'-AGCCTTCCA-GCTCCTTGAAGCA-3') (SEQ ID NO:40) and forward primer Universal Primer Short. PCR products were separated with 2% agarose gel electrophoresis, and DNA was extracted from gel with NucleoSpin Gel and PCR Clean-Up kit (Clontech). Thepurified PCR products were sequenced to determine identity.

Tumor RNAs were isolated and reverse transcribed into cDNA with an adaptor. By using nested PCR, the expected 166 bp of survivin and 106 bp of EGFR PCR products were resolved and visualized in agarose gels. Sequencing of PCR products confirm that cleavages present on the 10-nt from 5'-end of antisense strands of EGFR and survivin siRNAs. Therefore, PSEP mediated gene knockdown is through RNAi pathway.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A bivalent aptamer-siRNA chimera comprising:
   first and second ends, wherein the first and second ends comprise an aptamer that specifically binds a target protein; and
   an siRNA construct between the first and second ends, wherein the siRNA construct is processed by cellular RNAi machinery to produce at least two different siRNAs that specifically inhibit expression of two or more different genes in a cell expressing the target protein.

2. The chimera of claim 1, wherein the at least one of the two or more different genes are survivin and EGFR and the target protein is PMSA.

3. The chimera of claim 1, wherein the two or more different genes are oncogenes selected from the group consisting of ABL1, ABL2, AKT1, AKT2, ATF1, BCL11A, BCL2, BCL3, BCL6, BCR, BRAF, CARD11, CBLB, CBLC, CCND1, CCND2, CCND3, CDX2, CTNNB1, DDB2, DDIT3, DDX6, DEK, EGFR, ELK4, ERBB2, ETV4, ETV6, EVI1, EWSR1, FEV, FGFR1, FGFR1OP, FGFR2, FUS, GOLGA5, GOPC, HMGA1, HMGA2, HRAS, IRF4, JUN, KIT, KRAS, LCK, LMO2, MAF, MAFB, MAML2, MDM2, MET, MITF, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCL1A, TET2, TFG, MLL, TLX1, TPR, and USP6.

4. The chimera of claim 1, wherein the target protein is selected from the group consisting of CLPP, CEA, Her-2/neu, Bladder Tumor Antigen, Thyroglobulin, Alpha-fetoprotein, PSA, CA 125, CA19.9, CA 15.3, leptin, prolactin, osteopontin, IGF-II, CD98, fascin, sPIgR, EpCAM, transferrin receptor, CD44, AXL, Human matrix metalloprotease 9, VEGFR, EGFR, Her3, ICAM-1, VCAM-1, Chemokine receptors, CD3, CD4, CD8, TNFR, L (P,E) selectin, and 14-3-3 eta.

5. The chimera of claim 3, wherein the target protein is PMSA.

6. The chimera of claim 1, wherein the target protein is a tumor neovascular antigen.

7. A method for treating prostate cancer in a subject in need thereof, comprising:
administering to the subject and effective amount of the chimera of claim 2.

8. A method for killing cancer cells in a subject comprising:
administering an effective amount of a bivalent siRNA chimera to induce or promote apoptosis of the cancer cells, wherein the bivalent siRNA chimera comprises first and second ends, wherein the first and second ends comprise an aptamer that specifically binds a cell surface protein expressed by the cancer cells; and an siRNA construct (two or more tandem siRNAs) between the first and second ends, wherein the siRNA construct is processed by cellular RNAi machinery of the cancer cells to produce at least two different siRNAs that specifically inhibit expression of two or more different genes in the cancer cells to promote apoptosis of the cancer cells.

9. The method of claim 8, wherein the two or more different genes comprise survivin.

10. The method of claim 9, wherein the two or more different genes comprise an oncogene expressed by the cancer cell.

11. A method for reducing tumor burden in a subject in need thereof comprising:
administering to the subject an effective amount of a bivalent siRNA chimera to induce or promote apoptosis of the tumor cells, wherein the bivalent siRNA chimera comprises first and second ends, wherein the first and second ends comprise an aptamer that specifically binds a cell surface protein expressed by the tumor cells; and an siRNA construct between the first and second ends, wherein the siRNA construct is processed by cellular RNAi machinery of the cancer cells to produce at least two different siRNAs that specifically inhibit expression of two or more different genes in the tumor cells to promote apoptosis of the tumor cells and thereby reduce tumor burden in the subject.

12. A method of reducing tumor associated angiogenesis in a subject in need thereof comprising:
administering to the subject an effective amount of a bivalent siRNA chimera to reduce tumor associated angiogenesis, wherein the bivalent siRNA chimera comprises first and second ends, wherein the first and second ends comprise an aptamer that specifically binds a cell surface protein expressed by the tumor; and an siRNA construct between the first and second ends, wherein the siRNA construct is processed by cellular RNAi machinery of tumor to produce at least two different siRNAs that specifically inhibit expression of two or more different genes in the tumor, wherein the two or more different genes comprise EGFR and survivin.

13. A method for treating a viral infection in a subject comprising:
administering to the subject an effective amount of a bivalent siRNA chimera to inhibit expression genes of the virus infecting the subject, wherein the bivalent siRNA chimera comprises first and second ends, wherein the first and second ends comprise an aptamer that specifically binds a cell surface viral protein expressed by virally infected cells; and an siRNA construct between the first and second ends, wherein the siRNA construct is processed by cellular RNAi machinery of the cells to produce at least two different siRNAs that specifically inhibit expression of two or more different genes of the infecting virus.

14. A pharmaceutical composition comprising an effective amount of the bivalent siRNA chimera of claim 1.

15. The pharmaceutical composition of claim 14, wherein the bivalent aptamer-siRNA chimera comprises SEQ ID NOS: 1, 5, and 8.

* * * * *

UNITED STATES PATENT AND TRADEMARK OFFICE
CERTIFICATE OF CORRECTION

PATENT NO. : 10,689,654 B2  
APPLICATION NO. : 15/726851  
DATED : June 23, 2020  
INVENTOR(S) : Hong Yan Liu Page 1 of 1

It is certified that error appears in the above-identified patent and that said Letters Patent is hereby corrected as shown below:

In the Claims

In Claim 2, Column 47, Line 62, the abbreviation "PMSA" should read "PSMA".
In Claim 5, Column 48, Line 67, the abbreviation "PMSA" should read "PSMA".

Signed and Sealed this  
Third Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 35

<210> SEQ ID NO 1
<211> LENGTH: 64
<212> TYPE: RNA

<213> ORGANISM: artificial
<220> FEATURE:
<223> OTHER INFORMATION: synthetic construct

<400> SEQUENCE: 1
gggaggacga ugcggaucag ccauguuuac gucacuccua aaauguagag augcgguggu    60
ccuu                                                                64

<210> SEQ ID NO 2
<211> LENGTH: 64
<212> TYPE: DNA
<213> ORGANISM: artificial
<220> FEATURE:
<223> OTHER INFORMATION: synthetic construct

<400> SEQUENCE: 2
gggaggacga tgcggatcag ccatgtttac gtcactccta aaatgtagag atgcggtggt    60
cctt                                                                64

<210> SEQ ID NO 3
<211> LENGTH: 32
<212> TYPE: DNA
<213> ORGANISM: artificial
<220> FEATURE:
<223> OTHER INFORMATION: synthetic construct

<400> SEQUENCE: 3
taatacgact cactataggg aggacgatgc gg                                  32

<210> SEQ ID NO 4
<211> LENGTH: 40
<212> TYPE: DNA
<213> ORGANISM: artificial
<220> FEATURE:
<223> OTHER INFORMATION: synthetic construct

<400> SEQUENCE: 4
aaggaccacc gcatctctac attttaggag tgacgtaaac                          40

<210> SEQ ID NO 5
<211> LENGTH: 87
<212> TYPE: RNA
<213> ORGANISM: artificial
<220> FEATURE:
<223> OTHER INFORMATION: synthetic construct

<400> SEQUENCE: 5
gggaggacga ugcggaucag ccauguuuac gucacuccua aaaccuuagc agucuuaucu    60
aauuuuggac caccgcaucu cuacauu                                       87

<210> SEQ ID NO 6
<211> LENGTH: 87
<212> TYPE: DNA
<213> ORGANISM: artificial
<220> FEATURE:
<223> OTHER INFORMATION: synthetic construct

<400> SEQUENCE: 6
gggaggacga tgcggatcag ccatgtttac gtcactccta aaaccttagc agtcttatct    60
aattttggac caccgcatct ctacatt                                       87

<210> SEQ ID NO 7
<211> LENGTH: 30

<212> TYPE: DNA
<213> ORGANISM: artificial
<220> FEATURE:
<223> OTHER INFORMATION: synthetic construct

<400> SEQUENCE: 7
aatgtagaga tgcggtggtc caaaattaga                               30

<210> SEQ ID NO 8
<211> LENGTH: 21
<212> TYPE: RNA
<213> ORGANISM: artificial
<220> FEATURE:
<223> OTHER INFORMATION: synthetic construct

<400> SEQUENCE: 8
uuagauaaga cugcuaaggc a                                        21

<210> SEQ ID NO 9
<211> LENGTH: 38
<212> TYPE: DNA
<213> ORGANISM: artificial
<220> FEATURE:
<223> OTHER INFORMATION: syntehtic construct

<400> SEQUENCE: 9
taatacgact cactatatta gataagactg ctaaggca                      38

<210> SEQ ID NO 10
<211> LENGTH: 15
<212> TYPE: DNA
<213> ORGANISM: artificial
<220> FEATURE:
<223> OTHER INFORMATION: synthetic construct

<400> SEQUENCE: 10
taatacgact cacta                                               15

<210> SEQ ID NO 11
<211> LENGTH: 15
<212> TYPE: DNA
<213> ORGANISM: artificial
<220> FEATURE:
<223> OTHER INFORMATION: synthetic construct

<400> SEQUENCE: 11
tgccttagca gtctt                                               15

<210> SEQ ID NO 12
<211> LENGTH: 64
<212> TYPE: RNA
<213> ORGANISM: artificial
<220> FEATURE:
<223> OTHER INFORMATION: synthetic construct

<400> SEQUENCE: 12
gggaggacga ugcggaucag ccauguuuac gucacuccua aaaaacaguc gcguuugcga     60
cugg                                                           64

<210> SEQ ID NO 13
<211> LENGTH: 128
<212> TYPE: DNA
<213> ORGANISM: artificial
<220> FEATURE:
<223> OTHER INFORMATION: synthetic construct

```
<400> SEQUENCE: 13
gggaggacga tgcggatcag ccatgtttac gtcactccta aaaccagucg caaagcgcug      60
acacgggagg acgatgcgga tcagccatgt ttacgtcact cctaaaacca gucgcaaagc    120
gcugacac                                                             128

<210> SEQ ID NO 14
<211> LENGTH: 43
<212> TYPE: DNA
<213> ORGANISM: artificial
<220> FEATURE:
<223> OTHER INFORMATION: synthetic construct

<400> SEQUENCE: 14
gggaggacga tgcggatcag ccatgtttac gtcactccta aaa                       43

<210> SEQ ID NO 15
<211> LENGTH: 40
<212> TYPE: DNA
<213> ORGANISM: artificial
<220> FEATURE:
<223> OTHER INFORMATION: synthetic construct

<400> SEQUENCE: 15
ttgtcagcgc tttgcgactg gttttaggag tgacgtaaac                           40

<210> SEQ ID NO 16
<211> LENGTH: 21
<212> TYPE: DNA
<213> ORGANISM: artificial
<220> FEATURE:
<223> OTHER INFORMATION: synthetic construct

<400> SEQUENCE: 16
gtgtcagcgc uuugcgacug g                                               21

<210> SEQ ID NO 17
<211> LENGTH: 38
<212> TYPE: DNA
<213> ORGANISM: artificial
<220> FEATURE:
<223> OTHER INFORMATION: synthetic construct

<400> SEQUENCE: 17
taatacgact cactatagtg tcagcgcttt gcgactgg                             38

<210> SEQ ID NO 18
<211> LENGTH: 15
<212> TYPE: DNA
<213> ORGANISM: artificial
<220> FEATURE:
<223> OTHER INFORMATION: synthetic construct

<400> SEQUENCE: 18
taatacgact cacta                                                      15

<210> SEQ ID NO 19
<211> LENGTH: 16
<212> TYPE: DNA
<213> ORGANISM: artificial
<220> FEATURE:
<223> OTHER INFORMATION: synthetic construct

<400> SEQUENCE: 19
ccagtcgcaa agcgct                                                     16
```

<210> SEQ ID NO 20
<211> LENGTH: 62
<212> TYPE: RNA
<213> ORGANISM: artificial
<220> FEATURE:
<223> OTHER INFORMATION: synthetic construct

<400> SEQUENCE: 20
gggaggacga ugcggaucag ccauguuuac gucacuccuu uggaccaccg caucucuaca    60
uu                                                                  62

<210> SEQ ID NO 21
<211> LENGTH: 62
<212> TYPE: DNA
<213> ORGANISM: artificial
<220> FEATURE:
<223> OTHER INFORMATION: synthetic construct

<400> SEQUENCE: 21
gggaggacga tgcggatcag ccatgtttac gtcactcctt tggaccaccg catctctaca    60
tt                                                                  62

<210> SEQ ID NO 22
<211> LENGTH: 41
<212> TYPE: DNA
<213> ORGANISM: artificial
<220> FEATURE:
<223> OTHER INFORMATION: synthetic construct

<400> SEQUENCE: 22
aatgtagaga tgcggtggtc caaaggagtg acgtaaacat g                       41

<210> SEQ ID NO 23
<211> LENGTH: 64
<212> TYPE: RNA
<213> ORGANISM: artificial
<220> FEATURE:
<223> OTHER INFORMATION: synthetic construct

<400> SEQUENCE: 23
gggaggacga ugcggaucag ccauguuuac gucacuccua aaauuagaua agacugcuaa    60
ggca                                                                64

<210> SEQ ID NO 24
<211> LENGTH: 81
<212> TYPE: DNA
<213> ORGANISM: artificial
<220> FEATURE:
<223> OTHER INFORMATION: synthetic construct

<400> SEQUENCE: 24
taatacgact cactataggg aggacgatgc ggatcagcca tgtttacgtc actcctaaaa    60
ttagataaga ctgctaaggc a                                             81

<210> SEQ ID NO 25
<211> LENGTH: 40
<212> TYPE: DNA
<213> ORGANISM: artificial
<220> FEATURE:
<223> OTHER INFORMATION: synthetic construct

<400> SEQUENCE: 25
tgccttagca gtcttatcta attttaggag tgacgtaaac    40

<210> SEQ ID NO 26
<211> LENGTH: 61
<212> TYPE: RNA
<213> ORGANISM: artificial
<220> FEATURE:
<223> OTHER INFORMATION: synthetic construct

<400> SEQUENCE: 26
gggaggacga ugcggaucag ccauguuuac gucacguccu ccuuagcagu cuuaucuaau    60
u    61

<210> SEQ ID NO 27
<211> LENGTH: 61
<212> TYPE: DNA
<213> ORGANISM: artificial
<220> FEATURE:
<223> OTHER INFORMATION: synthetic construct

<400> SEQUENCE: 27
gggaggacga tgcggatcag ccatgtttac gtcacgtcct ccttagcagt cttatctaat    60
t    61

<210> SEQ ID NO 28
<211> LENGTH: 33
<212> TYPE: DNA
<213> ORGANISM: artificial
<220> FEATURE:
<223> OTHER INFORMATION: synthetic construct

<400> SEQUENCE: 28
aattagataa gactgctaag gaggacgtga cgt    33

<210> SEQ ID NO 29
<211> LENGTH: 86
<212> TYPE: RNA
<213> ORGANISM: artificial
<220> FEATURE:
<223> OTHER INFORMATION: synthetic construct

<400> SEQUENCE: 29
ggaucccgac uggcgagagc cagguacgaa uggauccaaa aaccuuagca gucuuaucua    60
auuuuggacc accgcaucuc uacauu    86

<210> SEQ ID NO 30
<211> LENGTH: 87
<212> TYPE: DNA
<213> ORGANISM: artificial
<220> FEATURE:
<223> OTHER INFORMATION: synthetic construct

<400> SEQUENCE: 30
ggatcccgac tggcgagagc caggtaacga atggatccaa aaaccttagc agtcttatct    60
aattttggac caccgcatct ctacatt    87

<210> SEQ ID NO 31
<211> LENGTH: 41
<212> TYPE: DNA
<213> ORGANISM: artificial
<220> FEATURE:
<223> OTHER INFORMATION: synthetic construct

<400> SEQUENCE: 31

```
-continued taatacgact cactatagga tcccgactgg cgagagccag g                    41

<210> SEQ ID NO 32
<211> LENGTH: 30
<212> TYPE: DNA
<213> ORGANISM: artificial
<220> FEATURE:
<223> OTHER INFORMATION: synthetic construct

<400> SEQUENCE: 32
aatgtagaga tgcggtggtc caaaattaga                                 30

<210> SEQ ID NO 33
<211> LENGTH: 62
<212> TYPE: RNA
<213> ORGANISM: artificial
<220> FEATURE:
<223> OTHER INFORMATION: synthetic construct

<400> SEQUENCE: 33
ggaucccgac uggcgagagc cagguaacga auggauccuu uuguagagau gcggugguccc   60 uu                                                               62

<210> SEQ ID NO 34
<211> LENGTH: 62
<212> TYPE: DNA
<213> ORGANISM: artificial
<220> FEATURE:
<223> OTHER INFORMATION: synthetic construct

<400> SEQUENCE: 34
ggatcccgac tggcgagagc caggtaacga atggatcctt ttgtagagat gcggtggtcc   60
tt                                                               62

<210> SEQ ID NO 35
<211> LENGTH: 31
<212> TYPE: DNA
<213> ORGANISM: artificial
<220> FEATURE:
<223> OTHER INFORMATION: synthetic construct

<400> SEQUENCE: 35
aaggaccacc gcatctctac aaaaggatcc a                               31
```